United States Patent [19]

Hargreaves et al.

[11] Patent Number: 5,345,943
[45] Date of Patent: Sep. 13, 1994

[54] APPARATUS FOR DETERMINING IN VIVO RESPONSE TO THERMAL STIMULATION IN AN UNRESTRAINED SUBJECT

[75] Inventors: Kenneth M. Hargreaves, Bethesda, Md.; Ronald Dubner, Washington, D.C.; Fred Brown, Rockville, Md.

[73] Assignee: The United States of America as represented by the Secretary of the Department of Health and Human Services, Washington, D.C.

[21] Appl. No.: 981,914

[22] Filed: Nov. 23, 1992

Related U.S. Application Data

[60] Continuation of Ser. No. 496,573, Mar. 21, 1990, abandoned, which is a division of Ser. No. 278,355, Dec. 1, 1988, Pat. No. 5,025,796.

[51] Int. Cl.[5] .............................................. A61B 5/00
[52] U.S. Cl. ..................................... 128/742; 128/743
[58] Field of Search .............................. 128/742–743, 128/736, 630, 897–898

[56] References Cited

U.S. PATENT DOCUMENTS

| | | |
|---|---|---|
| 3,304,911 | 2/1967 | Hakata et al. |
| 3,439,358 | 4/1969 | Salmons |
| 3,540,413 | 11/1970 | Castaigne et al. |
| 3,826,229 | 7/1974 | Class et al. |
| 3,935,485 | 1/1976 | Yoshida et al. |
| 3,970,862 | 7/1976 | Edelman et al. |
| 4,090,212 | 5/1978 | Byatt et al. |
| 4,115,692 | 9/1978 | Balcerak et al. |
| 4,337,726 | 7/1982 | Czekajewski et al. |
| 4,574,734 | 3/1986 | Mandalaywala et al. |

OTHER PUBLICATIONS

Siegmund et al., "A Method for Evaluating both Non--Narcotic and Narcotic Analgesics", PSEMB v. 95 (1957).
Eddy et al., "Synthetic Analgesics II. Dithienylbutenyl- and Dithienylbutylamines", National Institute of Arthritis and Metabolic Diseases, pp. 385–393 (1952).
D'Amour et al., "A Method for Determining Loss of Pain Sensation", The Biologic Research Laboratory, pp. 74–79, (1941).
Ercoli et al., Studies on Analgesics, The Research Laboratories, Hoffman La–Roche, pp. 301–317.
Joris, J., Dubner, R., Brown, F., Flores, C., and Hargreaves, K.: "Behavorial and Endocrine Correlates of Thermal Nociception in Carrageenin–Induced Cutaneous Hyperalgesia", Abs. Soc. Neurosci. 1986.
Joris, J., Dubner, R., and Hargreaves, K.: "Involvement of the Peripheral Nervous System in Carrageenan–Induced Inflammation", Abs. Soc. Neurosci. 1987.
Hargreaves, K. and Joris, J.: "Opiates Suppress Carrageenan–Induced Inflammation", Abs. Soc. Neurosci. 13: 1017, 1987.
Costello, A. H., and Hargreaves, K. M.: "Peptide Analogs of Bradykinin (BK) Inhibit Carrageenan–Induced Inflammation", America Pain Society Abstract #SS 2d, 1988. Toronto, Canada.

(List continued on next page.)

Primary Examiner—Lee S. Cohen
Assistant Examiner—John P. Lacyk
Attorney, Agent, or Firm—Lowe, Price, LeBlanc & Becker

[57] ABSTRACT

An apparatus for determining in vivo hyperalgesia to thermal stimulation in an unrestrained subject within a predetermined space permitting the selective application of radiant heat to a site of the subject comprises a timer, a movable light source, a light detector and a stopper for the timer, the light source and the detector, the stopper being electrically connected thereto and automatically activated by the light detector upon site withdrawal, and a starter for the timer and the light source and for activating the light detector that is electrically connected thereto. When the light source is aimed at the site and positioned at a distance effective to locally provide radiant heat thereto and the starter is activated, after a latency time period the light beam elicits a spontaneous withdrawal response from the subject that is detected by the detector. The timer, the light source and detector, the stopper and the starter are part of an electrical circuit which is to be connected to a power source prior to use.

8 Claims, 3 Drawing Sheets

OTHER PUBLICATIONS

Hargreaves, K. M., Joris, J. and Dubner, R.: "Peripheral Actions of Opiates in the Blockade of Carrageenan-Induced Cutaneous Hyperalgesia", Pain (Suppl. 4): S17, 1987 Hamburg, Fed. Rep. of Germany.

Hargreaves, K. M., Carson, D. and Costello, A.: "Corticotropin Releasing Factor (CRF) Analgesia: Evaluation of Pituitary and Adrenal Gland Mediation", Abst. Submitted for the 1989 meeting of the American Association for Dental Research 1989.

J. L. Joris, MD, R. Dubner, DDS, PhD, and K. M. Hargreaves, DDS, PhD "Opioid Analgesia at Peripheral Sites: A Target for Opioids Release during Stress and Inflammation?" ANESTH ANALG 1987; 66:1277-81.

Kenneth M. Hargreaves, Ronald Dubner and Jean Joris, "Peripheral actions of opiates in the blockade of carrageenan-induced inflammation" 1988.

Robert I. Taber, "Predictive Value of Analgesic Assays in Mice and Rats" pp. 191-211.

Kenneth M. Hargreaves, Ann H. Costello and Jean L. Joris, "Release From Inflames Tissue of a Substance with Properties Similar to Corticotropin Releasing Factor" Manuscript 88-118 revised.

K. Hargreaves, R. Dubner, F. Brown, C. Flores and J. Joris, "A new and Sensitive method for measuring thermal nociception in cutaneous hyperalgesia" Pain, 32 (1988) 77-88 (Basic Section).

K. Hargreaves, Emanuel S. Troullos, Raymond A. Dionne, Elizabeth A. Schmidt, Susan C. Schafer and Jean Joris, "Bradykinin is increased during acute and chronic inflammation: Therapeutic implications" Dec. 88 Issue of Clin, Pharm. Ther.

Eaden F. Keith, "Evaluation of Analgesic Substances" American J. Pharm. 132: 202-230 (1960).

G. Woolfe and A. D. MacDonald, "The Evaluation of the Analgesic Action of Pethidine Hydrochloride (Dermerol)", J. Pharmacology and Experimental Theropeutics 80, 300-307 (1944).

Lowell O. Randall and Joseph J. Selitto, "A Method for Measurement of Analgesic Activity on Inflamed Tissue" Arch. int. pharmacodyn., 1957, CXI, No. 4.

S. H. Ferreira, "Prostaglandins, Aspirin-like Drugs and Analgesia", Nature New Biology 240:200-203 (1972).

Weiner et al, "Neurohumoral Transmission: The Autonomic and Somatic Motor Nervous System", in The Pharmacological Basis of Therapeutics, Gilman & Goodman, N.Y., McMillan Publishers, 7ED p. 505 (1985).

Levine et al, "Noradrenaline Hyperalgesis is Mediated Through Interaction with Sympathetic Post-ganglionic Neurone Terminals Rather than Activation of Primary Afferent Nociceptors", Nature 323:158-169, (1986).

Hermens, et al, "Comparison of Histamine Release in Human Skin Mast Cells Induced by Morphine, Fentanyl & Oxymorphone", Anesthesiology 62:124-129 ('85).

5,345,943

APPARATUS FOR DETERMINING IN VIVO RESPONSE TO THERMAL STIMULATION IN AN UNRESTRAINED SUBJECT

This application is a continuation of application Ser. No. 07/496,573, filed Mar. 21, 1990, now abandoned; which is a division of application Ser. No. 07/278,355, filed Dec. 1, 1988, now U.S. Pat. No. 5,025,796.

TECHNICAL FIELD

This invention relates to a high sensitivity apparatus for determining the in vivo response to thermal stimulation in an unrestrained subject within a predetermined space comprising time measuring means, movable means for generating a light beam, light beam detecting means, stopping means starting means, the time measuring means, generating means, detecting means, stopping means and starting means being part of an electrical circuit which is to be connected to a power source prior to use. This invention also relates to a high sensitivity in vivo method of discerning a peripherally-mediated response to thermal stimulation caused by a drug in an unrestrained subject which comprises administering the drug to a first situs, locally applying radiant heat to the situs to produce, after a latency period, withdrawal thereof in the absence of the drug, measuring the latency time period for withdrawal in the presence of the drug, administering a placebo to a second situs contralateral to the first situs, measuring the placebo withdrawal latency time period and subtracting the drug withdrawal latency time period from the placebo latency time, whereby if the difference is less than about one second the drug is said to act substantially like the placebo, if the difference is about one second or greater the drug is said to produce peripherally mediated hyperalgesia and if the difference is about minus one second or less the drug is said to produce hypoalgesia. This invention also relates to a high sensitivity in vivo method of determining the response to thermal stimulation caused by a drug in an unrestrained subject by administering a placebo to the subject, heating a situs of the subject and measuring the withdrawal latency time period elapsed before withdrawal occurs, administering the drug, measuring the drug withdrawal latency time period and subtracting this value from the placebo time period, whereby if the difference is less than about one second the drug is said to act substantially like the placebo, if the difference is about one second or greater the drug is said to produce hypoalgesia and if the difference is about minus one second or less the drug is said to produce hyperalgesia. This invention also relates to a high sensitivity in vivo method of discerning a peripheral response to thermal stimulation in an unrestrained subject by heating a situs of a subject to produce spontaneous situs withdrawal and measuring the withdrawal latency time period elapsed until withdrawal, heating a second situs which is contralateral to the first situs with a similar amount of radiant heat and measuring a second withdrawal latency time period, and comparing the first and the second time periods, whereby if the difference is about one second or greater the situs with the lower latency period is set to be afflicted with peripheral hyperalgesia with respect to the other side.

BACKGROUND ART

The main function of analgesia is to alleviate pain or suppress its perception in a subject.

Pain can be defined in a variety of ways. One of them establishes pain as the perception by a subject of noxious stimuli which produces a withdrawal reaction by the subject. A variety of methods have long been available for the evaluation of subject's response to pain. In general, these experimental procedures must comply with several criteria in order to be of use. The effect to be measured must be unequivocally related to the pain experimented by the subject. The applied stimulus must produce a reproducible and measurable response, and ideally the response should be a single response. However, rarely do methods comply with the latter requirement.

It is recognized that there are at least two modes of pain known as pricking and burning pain. The sensation of pricking pain is one that reaches a sharp peak and subsides quickly while the one of burning pain has a slower onset, rises gradually, then plateaus but never reaches the same type of peak or intensity observed with pricking pain, and lasts for a longer period of time (Keith E. F., Amer. J. Pharm. 132:212-230 (1960)).

Pain has also been classified in accordance with other criteria (Pfeiffer, C. C. et al, Ann. N. Y. Acad. Sci. 51:21 (1948)). "Supain" is used to describe superficial pain and is similar to the previously referred to as pricking pain. It can easily be elicited by pricking the skin with a needle. The second type of pain is "deepain" which is of an aching character. An example of this type is a tooth ache. Lastly, another type of pain is "sympain" which is exemplified by migraine headaches and is typically felt in the vessels of the temporal region. This pain is relieved by ganglionic blockade. The levels at which pain may be blocked are the receptors themselves. Many agents which block pain by acting superficially do so at the receptor itself. A second way of acting is that where the agents act at the internuncial pool of the spinal cord by blocking pain or raising the threshold for synaptic transmission. Centrally, the thalamus of the brain may also be involved in suppressing pain, or the cortex of the brain may be obtunded. Some analgesic agents may suppress muscle and joint pain. An example of these agents is salicylic acid which relieves pain from deep structures in muscular joint areas.

In order to study the mechanism of action of the different available drugs as well as novel drugs which are constantly being developed there is a broad background of techniques from which to select. However, all the available techniques have some beneficial and some detrimental characteristics. In general, the techniques can be divided into five groups:

1) Chemical methods
2) Electrical methods
3) Mechanical methods
4) Thermal methods and
5) Pharmacological methods 1) Chemical Methods In general these methods rely on the application of a chemical compound to the skin of a subject. The simpler methods rely on the immersion of a part of the subject in a chemical which causes irritation to the skin. In another method the chemical irritant is administered subcutaneously. A more sophisticated method is one where a writhing agent is inserted in the peritoneal cavity of an animal and produces a characteristic writhing response which occurs five or more times in a period of 10 minutes immediately following the administration of the chemical (Siegmund et al, Proc. Soc. Exptl. Biol. Med. 95:729 (1957)). In general this type of method shows a lack of specificity in the response of the animals. It is unclear whether it is the irritation produced by the administered chemical or the release of some substance which is responsible for the observed effects.

2) Electrical Methods

The more primitive of these type of methods promote the painful stimulation of the skin to produce pain. In general the end point of this method is not sufficiently specific. A variation of this technique involves the application of an electrical current to the rat's scrotum by means of platinum electrodes. The current is increased until the animal squeals. Yet another electrical method is that where an electric current is applied to the pulp of a tooth (Koll, W. and Reffert, H., Arch. Exptl. Pathol. Pharmakol 190:687 (1938)). A modified version of this technique, and currently utilized, consists of delivering to an inlaid filling in a vital tooth a shock at various levels of intensity to determine the threshold of pain with and without a drug. This method has also been applied to humans. This method has the limitation imposed by the proximity of the filling to the pain receptors. In addition, different animals have different responses to the electrical stimulation of the pulp of the tooth and the responses are not always correlatable. The subject must be thus carefully watched and the electrodes require careful attachment for maintaining good electrical contact throughout the testing.

3) Mechanical Methods

The evaluation of the results of these methods is substantially subjective and does not permit the ready quantification thereof. These methods are therefore only applied in general to the primary screening of pain. Surgical blades adapted in various manners are utilized in the most primitive of these methods to produce a pain reaction. The blade is applied with a graded forceps and the amount of pressure necessary to elicit pain is expressed as the number of steps required in order to produce a squeak in the experimental animal. The pressure exercised by the blades of the forceps has also been measured by placing a dynamometer therebetween or between the handles of the forceps. Artery clamps or clips have also been utilized instead of forceps. In humans, mechanical pressure has been applied over bone structures or by eliciting visceral pain such as in the enteric canal or in the esophagus by introducing and inflating balloons therein. The amount of pressure required to produce pain can be measured by means of a manometer but the subject itself is the one to report the degree of pain. A more modern version of the method is that described by Randall-Selitto (Randall, L. O., and Selitto J. J., Arch. Int. Pharmacodyn CXI (4):409 (1957)). The pain threshold is measured in this method as the amount of pressure in mmHg required to induce a flight reaction (struggle) when applied to the foot of an experimental animal. Air pressure from an air line is admitted through a needle valve to a syringe into a pressure gauge which is connected by a T-tube. The syringe is mounted with a plunger downward, to which is connected a short bullet-shaped wooden peg. The pressure is applied through the wooden tip to the plantar surface of the rat's foot at a specified rate of mm Hg per second. The end point is said to have been reached when the rat starts struggling, as subjectively determined by an observer. The Randall-Selitto method has various drawbacks, including the fact that the mechanical stimuli activate both low and high threshold mechanoreceptive nerves in both cutaneous and non-cutaneous tissue, it requires that the experimental animal be restrained during the testing period, exhibiting therefore only limited behavioral movement and suffering from activation of stress-related physiologic responses such as sympatho-drenomedulary and pituitary-adrenal mediated stress responses, and the high degree of inaccuracy because of the subjective determination by an observer of the end point of the animal's response.

4) Thermal Methods

The simplest form of these methods is the hot plate technique originally described by Woolfe and McDonalds (Woolfe, G. and McDonalds, A. D. J. Pharmacol. Exptl. Therap. 80:300 (1944)). Originally, this method utilized a zinc plate with a lamp placed underneath. In a later modification it uses an electric lamp as the source of heat and a copper plate for the conduction of heat (Eddy, N. B. and Leimbach, D., J. Pharmacol EXPTL. Therap. 107:385 (1953)). The first sign of discomfort is usually expressed as an attempt to sit up and lick the forepaws by the experimental animal. This is taken to be an indication of a threshold under the predetermined conditions. Dancing and jumping about by an undrugged animal is taken as an indication of unbearable pain whereas drugged animals more commonly withdraw the hind paws and keep them close to their abdomen. Although widely used, this technique is also only recommended as a preliminary screening one because all points of contact between the animal and the hot plate are subjected to heat and the end-point is also determined subjectively by an observer. A hot wire technique consists of the application of heat from a wire coiled inside an asbestos plate. The animal's tail is placed in a channel made in the plate (Davis, O. L. et al, Brit. J. Pharmacol 1:255 (1946)). Yet another thermal method utilizing light from a headlamp focused on the tip of the tail of an animal (D'Amour, F. E., and Smith, D. L., J. Pharmacol. EXPTL. Therap. 72:74 (1941)). This method measures the time between the application of the heat and the flick of the tail and has therefore been called the "tail flick" method. With this method it is only possible to detect analgesic effects with large doses of chemical compounds such as aspirin and aminopyrine. However, these large doses only elicit a slight degree of analgesia. In general it is considered that this method is solely satisfactory for the detection of potent analgesics (e.g., opiates such as morphine) but unsatisfactory when applied to medium or weak analgesic agents. A further thermal method utilizes a light bulb focused on the loin of an animal which is protected by a plexiglass shield having a port and a shutter positioned between a lens and the animal. When the shutter is opened the timer starts and when the animal reacts the shutter is closed and the timer stopped (Ercoli, N., and Lewis, M. N., J. Pharmacol. EXPTL. Therap. 84:301 (1945)). This method applies an incident light the strength of which can be varied by means of a rheostat. This method is good for detecting potent analgesic substances but has the drawback that it only applies heat to one point of the body and the end-point is subjectively determined by an observer which operates the shutter and starts the timer. Weaker analgesic compounds such as aspirin show no effect when pain is measured by this method.

5) Pharmacological Methods

Typical representatives of this group are methods which rely on the administration of a substance to produce a rise in the temperature of an experimental animal. The skin temperature or the core temperature may be utilized. Yeast is a good example of a substance which can be used for producing an increase in temperature. The ability of a compound to inhibit this induced rise in temperature has been used as a means for evaluating antipyretic analgesic activity. In fact, the Randall-Selitto method described above (Randall, L. O. and Selitto, J. J., supra) is a combination of a mechanical method for evaluating analgesia and a physiological response method. It combines the administration of yeast as a phlogistic in the plantar surface of one paw of a rat and the use of a pressure device for eliciting a response. The threshold in the foot that has been injected with the yeast suspension drops to less than one half that of the control foot one hour after the injection of yeast.

An exhaustive comparison of the various method's known in the art was made by Taber (Taber, R. I., "Predictive Value of Analgesic Assays in Mice and Rats, in Narcotic Antagonists", edited by Braude et al, Advances in Biochemical Phytopharmacology, vol. 8, Raven Press, New York (1974), p. 191)). The scoring of most of the major techniques according to the methods rating scales are listed in the following table taken from Taber (Taber, R. I., supra) and are meant to provide a summary of the foregoing discussion.

TABLE 1

Comparison of analgesic tests by rating scale

| Criteria* | Thermal | | Mechanical | | Chemical | Electric | |
|---|---|---|---|---|---|---|---|
| | Mouse hot-plate | Rat tail-flick | Mouse tail-flick | Rat paw yeast | Mouse writhing | Rat flick-jump | Mouse tail-shock |
| Sensitivity | | | | | | | |
| a | 2 | 4 | 2 | 4 | 4 | 4 | 3 |
| b | 2 | 2 | 1 | 3 | 4 | 3 | 3 |
| c | 2 | 1 | 2 | 1 | 0 | 2 | 1 |
| d | 1 | 2 | 0 | 2 | 2 | 2 | 2 |
| Simplicity | | | | | | | |
| a | 2 | 2 | 2 | 2 | 2 | 0 | 1 |
| b | 2 | 2 | 2 | 1 | 2 | 0 | 1 |
| Reproducibility | 4 | 4 | 4 | 4 | 4 | 1 | 2 |
| Total Score | 15 | 17 | 13 | 17 | 18 | 12 | 13 |

*See Table 2.

The electrical methods, while promising, are of substantially no use because they lack simplicity and reproducibility. The remaining methods, however, score low in terms of sensitivity. General criteria for the scoring of the various methods are listed in Table 2 provided hereinbelow which has also been obtained from Taber (Taber, R. I., supra).

TABLE 2

Analgesic method criteria rating scale

| Criteria | Score | | |
|---|---|---|---|
| Sensitivity | | | |
| a. Is it sensitive to known analgesics? | 1 for each class | 4 (max. score) | |
| b. How sensitive is it to doses in the clinical range? | Median of drug sensitivity | 4 (max. score) | |
| | No | Questionable | Yes |
| c. Is it insensitive to nonanalgesics? | 0 | 1 | 2 |
| d. Is there an established, clear-cut relationship between intensity and end point? | 0 | 1 | 2 |
| Simplicity | | | |
| a. Does it require technical expertise? | 0 | 1 | 2 |
| b. Does it require sophisticated instrumenta- | 0 | 1 | 2 |

TABLE 2-continued

Analgesic method criteria rating scale

| Criteria | Score | |
|---|---|---|
| tion? | | |
| Reproducibility | | |
| How many laboratories have successfully used the technique | 0-4 | 4 |

In general, the mouse writhing and the Randall-Selitto methods can detect antiinflammatory drugs. However, they do not provide for the automated detection of the end-point signal and are subject to substantial observer bias. On the other hand the rat tail flick method has an automated end-point but is very insensitive to various drugs such as antiinflammatory drugs, it lacks a within animal design and tests a particularly insensitive type of skin such as the one occurring in the tail of an animal. This type of skin is scaly and not very responsive to thermal stimulation.

Thus, despite the advantages of the various thermal stimulation methods (Dubner, R., et al, "Responses of Facial Cuntoneous Thermosensitive and Mechenosensive Afferent Fibers in the Monkey to Noxious Heat Stimulation", Adv. Neurol 4:61-71 (1974)), no good behavioral method exists for the quantitation of thermal nociception of hyperalgesia in a subject such as an animal model. The only method capable of quantitating behavioral responses to cutaneous hyperalgesia has been the Randall-Selitto method described above. This method has the various already indicated drawbacks. In addition, this method does not permit the simultaneous measurement of parameters other than the nociceptive threshold in the experimental animal.

Accordingly, there is still a need for a novel and simple method for the qualitative and/or quantitative in vivo measurement of responses to thermal stimulation in an unrestrained subject which overcomes the drawbacks of the prior art methods. Such method should ideally provide an automated detection of the subject's behavioral end-point, permit the use of unrestrained and unstressed animals, and optionally a within subject control, all of which and in the removal of observer bias and between animal variation while providing a powerful tool for distinguishing between centrally mediated and peripherally mediated responses to thermal stimulation.

Disclosure of the Invention

This invention relates to a high sensitivity apparatus for determining the in vivo response to thermal stimulation in an unrestrained subject within a predetermined space which permits the selective application of radiant heat to a predetermined situs of the subject by means of a light beam, the combination comprising means for measuring time;

movable means for generating a light beam;

means for detecting said beam, said detecting means being positioned so that it can detect the withdrawal of the situs from the path of said light beam and said detecting means also being isolated from said light beam generating means;

means for stopping said time measuring means and said light beam generating means and for inactivating said detecting means, all said means being electrically interconnected, said stopping means being automatically activated by said detecting means upon situs withdrawal;

means for simultaneously starting said time measuring means and said light beam generating means and for activating said detecting means, all said means being electrically interconnected, whereby when said light generating means is aimed at the predetermined situs and positioned at a distance effective to locally provide radiant heat to said situs and said starting means is activated, the light beam elicits from said subject after a latency time period a spontaneous situs withdrawal response thereof which is detected by said detecting means, said time measuring means, said generating means, said detecting means, said stopping means and said starting means being part of an electrical circuit which is to be connected to a power source prior to use.

This invention also relates to a high sensitivity in vivo method of discerning a peripherally-mediated response to thermal stimulation caused by a drug in an unrestrained subject, comprising (a) administering a drug to said subject for local delivery to a first situs thereof;

(b) exposing said situs to an amount of radiant heat effective to produce situs withdrawal after a latency time period in the absence of said drug;

(c) allowing said subject to spontaneously withdraw said situs from said radiant heat which is immediately discontinued;

(d) measuring the withdrawal latency time period elapsed between steps (b) and (c);

(e) administering a placebo to a second situs of said subject, said second situs being contralateral to said first situs and not being affected by said drug;

(f) repeating steps (b) through (d); and (g) subtracting said drug withdrawal latency time period from said placebo latency time period, whereby if the difference is less than about 1 second the drug is said to act substantially like the placebo, if the difference is about 1 second or greater the drug is said to produce peripherally mediated hyperalgesia, and if the difference is about −1 second or less the drug is said to produce peripherally-mediated hypoalgesia.

This invention also relates to a high sensitivity in vivo method of determining the response to thermal stimulation caused by a drug in an unrestrained subject, comprising (a) administering a placebo to said subject;

(b) exposing a predetermined situs of said subject to an amount of radiant heat effective to produce situs withdrawal after a latency time period;

(c) allowing for said subject to spontaneously withdraw the situs from the heat beam;

(d) measuring the withdrawal latency time period elapsed between steps (b) and (c);

(e) administering the drug to said subject;

(f) repeating steps (b) through (d); and (g) subtracting said drug withdrawal latency time period from said placebo withdrawal latency time period, whereby if the difference is less than about 1 second the drug is said to act substantially like the placebo, if the difference is about 1 second or greater the drug is said to produce hyperalgesia and if the difference is about −1 second or less the drug is said to produce hyperalgesia.

Also part of this invention is a high sensitivity in vivo method of discerning a peripherally-mediated response to thermal stimulation caused by a second drug in an unrestrained subject, after administration of a first hyperalgesic drug comprising (a) administering a first drug to said subject for local delivery to a first situs thereof;

(b) exposing said situs to an amount of radiant heat effective to produce situs withdrawal after a latency time period in the absence of said first drug;

(c) allowing said subject to spontaneously withdraw said situs from said radiant heat which is immediately discontinued;

(d) measuring the withdrawal latency time period elapsed between steps (b) and (c);

(e) administering a placebo to a second situs of said subject, said second situs being contralateral to said first situs and not being affected by said first drug;

(f) repeating steps (b) through (d); and (g) subtracting said first drug withdrawal latency time period from said placebo latency time, whereby if the difference is less than about 1 second the first drug is said to act substantially like the placebo, if the difference is about 1 second or greater the first drug is said to produce peripherally mediated hyperalgesia, and if the difference is about −1 second or less the first drug is said to produce peripherally-mediated hypoalgesia;

administering to said subject a second drug suspected of countering the hyperalgesic effect of first drug tested;

(i) repeating step (f); and (j) subtracting said first drug withdrawal latency time period from said second drug withdrawal latency time period to obtain a first coefficient, and subtracting said second drug withdrawal latency time period from said placebo withdrawal latency time period to obtain a second coefficient, whereby if the first coefficient is between about −1 and 1 it is said that the second drug fails to significantly change the effect of the first drug, if the first coefficient is about −1 sec or less the second drug is said to further enhance the hyperalgesic effect of the first drug, if the first coefficient is about 1 second or greater but less than about the value of the second coefficient the second drug is said to cause hypoalgesia, and if the first coefficient is greater than about the second coefficient the second drug is said to cause analgesia, and whereby if the second drug is administered for local delivery to the same situs as the first drug, the second drug is said to cause a peripherally-mediated effect.

Also part of this invention is a high sensitivity in vivo method of discerning a peripheral response to thermal stimulation in an unrestrained subject, which comprises (a) exposing a first situs of said subject to an amount of radiant heat effective to produce situs withdrawal;

(b) allowing said subject to spontaneously withdraw said situs from said radiant heat which is immediately discontinued;

(c) measuring the withdrawal latency time period elapsed between steps (a) and (b);

(d) exposing a second situs of said subject to a similar amount of radiant heat used in step (a), said second situs being contralateral to said first situs;

(e) repeating steps (b) and (c); and (f) comparing said first situs withdrawal latency time period with said second situs withdrawal latency time period, whereby if the difference is less than about one second both situses are said to act equivalently and if the difference is about 1 second or greater the situs with the lower latency period is said to be afflicted with peripheral hyperalgesia with respect to the other side.

A more complete appreciation of the invention and many of the attendant advantages thereof will be readily perceived as the same becomes better understood by reference to the following detailed description when considered in connection with the accompanying figures.

Figure 1:
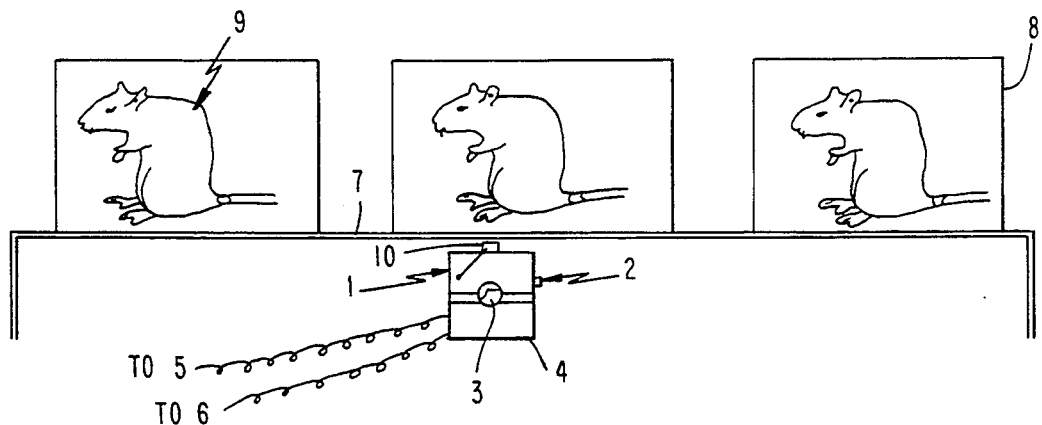
FIG. 1 provides a schematic description of one embodiment of the apparatus of the invention. A light detecting means (1) is aimed at an aperture (10) located in a movable enclosure (4) also containing a light beam generating means (3). On the movable enclosure (4) is also located a means for starting (2) a time measuring means (6) not shown in the figure. The circuit connecting the various components in the movable box is electrically connected to a power supply (5) not shown in the drawing. The movable enclosure (4) is placed underneath a base (7) which permits the passage of the light beam to reach an experimental animal (9) placed on its top surface. Once the animal is placed on the base an enclosure (8) which permits the visualization of events occurring therewithin is placed over the animal (9) and leaned on the base (7).
Figure 2:
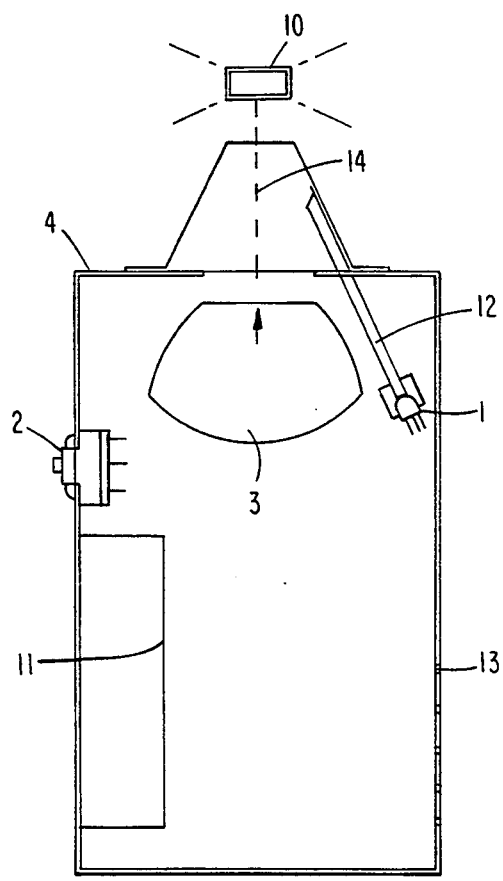
FIG. 2 is a schematic representation of the apparatus and it shows the detecting means (1) which is protected by an insulating means (12) so that it will not detect the heat or light of the light beam generating means (3) because of its proximity. The movable enclosure (4) is shown as a screen or an enclosure containing holes (13) for ventilation purposes. An electronic circuit and LED readout (11) for the output signal of the time measuring device (not shown in the drawing) are depicted. The starting means (2) is shown attached to the enclosure (4) of the movable enclosure. Finally, a window or aperture (10) is shown which permits the passage of the light beam (14) generated by the generating means (3).

Other objects, advantages and features of the present invention will become apparent to those skilled in the art from the following discussion.

BEST MODE FOR CARRYING OUT THE INVENTION

This invention arose from a desire to improve over prior art methods for measuring the response to pain in subjects such as experimental animals and humans. The present inventors particularly desired to improve over prior art methods which lack objectivity in the determination of the end-point response by the subject, required that the subject be restrained during the tests, activate different pain response mechanisms and do not permit the measurement of other parameters during the determination of the subject's response to thermal stimulation. In addition to relying on the utilization of an unrestrained subject, providing for the objective determination of the end-point response and relying on the activation of a single response mechanism to thermal stimulation, the present method clearly affords superior bioassay sensitivity when compared with the prior art methods and permits the measurement of several other behavioral responses in addition to the withdrawal latency time period.

The apparatus provided by this invention is a high sensitivity apparatus for determining in vivo hyperalgesia to thermal stimulation in an unrestrained subject within a predetermined space. This method permits the selective application of radiant heat to a predetermined situs of the subject by means of a light beam and comprises a combination of means for measuring time;

movable means for generating a light beam;

means for detecting said beam, said detecting means being positioned so that it can detect the withdrawal of the situs from the path of said light beam and positioned so that it is isolated from said light beam generating means;

means for stopping said time measuring means and said light beam generating means and for inactivating said detecting means, all said means being electrically interconnected and said stopping means being automatically activated by said detecting means upon situs withdrawal;

means for simultaneously starting said time measuring means and said light beam generating means and for activating said detecting means, all said means being electrically interconnected, whereby when said light generating means is aimed at the predetermined situs and positioned at a distance thereof effective to locally provide radiant heat to said situs and said starting means is activated, the light beam on the situs elicits after a latency time period a spontaneous situs withdrawal response thereof from said subject which is detected by said detecting means, said time measuring means, said generating means, said detecting means, said stopping means and said starting means being part of an electrical circuit which is to be connected to a power source prior to use.

In a particular embodiment of the invention the means for measuring time may be a simple clock, a timer or other means for measuring time which may simply have a display showing the final value of the withdrawal latency time period for each determination. The means for measuring time may, however, also be directly connected to a means for receiving and storing an output signal produced therefrom. The storage means may be in the form of a computer memory, discs such as floppy or hard discs, tapes, cards, a printout and the like. Different means for receiving and storing output signals are known in the art as are the means for connecting them to a means for detecting time.

The apparatus of the invention may also further comprise a computing means for comparing successively obtained output signals received from said time measuring means. Software packages for conducting such comparisons and providing a printed output of the results are commercially available and/or are easily devised for a particular computing system.

In another particular embodiment of the invention the apparatus further comprises a means for receiving and displaying an output signal of the time measuring means. Displaying means such as those utilizing TV screens and the like are known in the art as the means for coupling them with the time measuring means.

Figure 4:
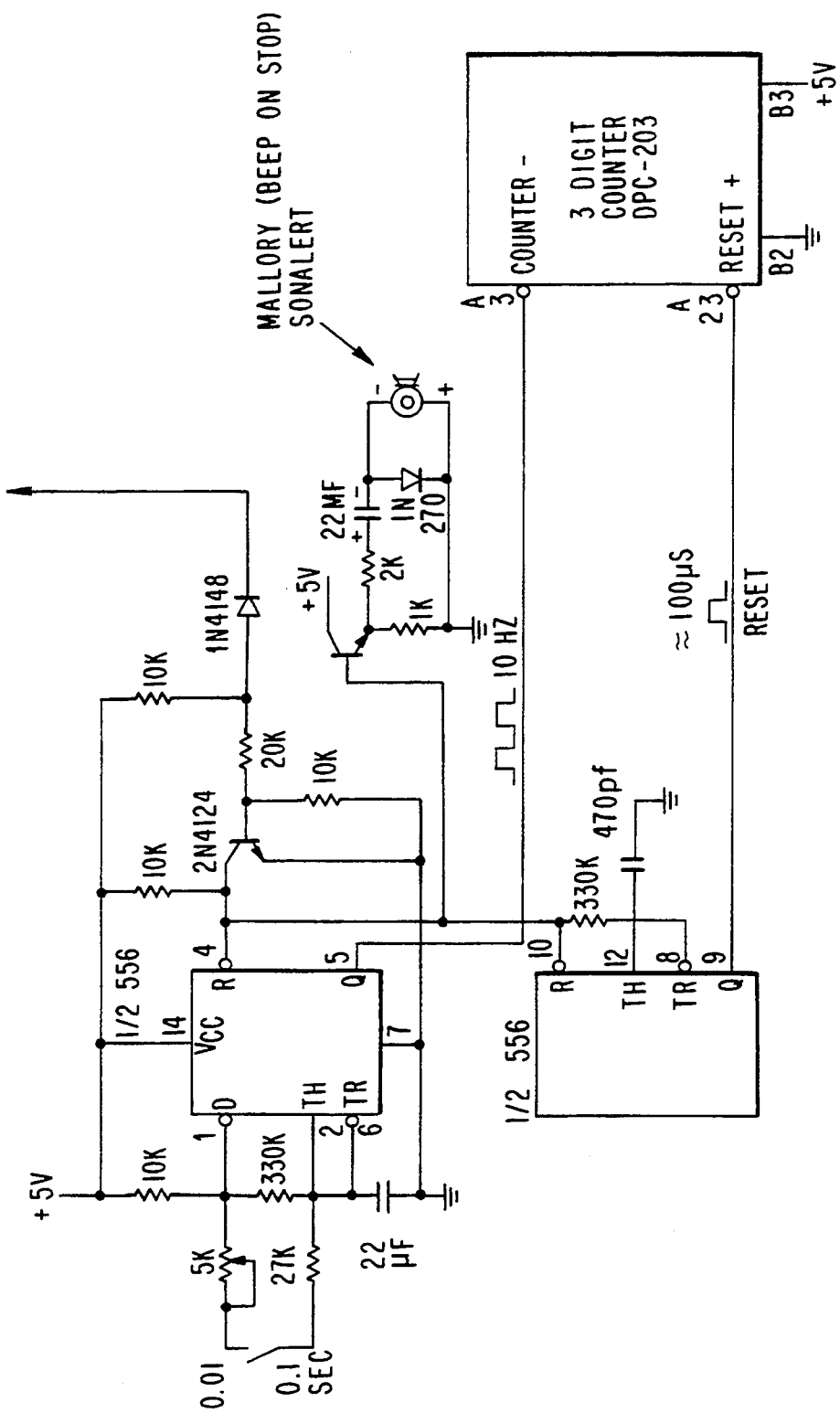
FIG. 4 shows a schematic representation of one embodiment of the time measuring means in accordance with this invention.

By means of example, the circuitry for a particular embodiment of the time measuring means of the invention is shown in FIG. 4 attached hereto. In another particular embodiment of the invention the apparatus described herein has its electrical circuitry connected to a power supply of direct current providing about 0.1 to 10 volts and about 0.1 to 10 amps, and more preferably about 5.5 to 8.5 and about 9.5 to 10.5 amps.

In another preferred embodiment the light beam generating means of the apparatus of the invention is a focused light bulb of about 1 to 120 volts and about 25 to 200 watts and more preferably about 6 to 20 volts and about 20 to 60 watts.

By means of example the light detecting means may be a phototransistor. However, other known light detecting means may also be utilized with the present apparatus.

In a particularly preferred embodiment of the invention which can be utilized for determining the response to thermal stimulation in experimental animals, the apparatus of the invention further comprises a movable container wherein the light beam generating means, the detecting means and the stopping means are located, the movable container being provided with a light beam window and the light beam generating means being positioned so that the beam travels in the direction of the window and through it. The starting means may be provided to be accessible from without the container in order that the operation of the apparatus may be easily started, preferably manually.

In another particularly preferred embodiment of the invention the enclosure containing the light generating means, the detecting means, the stopping means and the starting means is of a size ranging from about 2 to 8 in diameter, and more preferably about 3 to 4 in diameter. Typically, the enclosure will have a flat base so that it may rest on a surface once it is positioned so that the light beam generating means is focused on the predetermined situs of the subject. By means of example the movable enclosure may be a box or have other forms which may be laid on a surface.

The enclosure typically has a window permitting the passage of the light beam generated therewithin. The window has a typical width of about 2 mm to 20 mm and about 1 mm to 10 mm in length, and more preferably about 3 to 6 mm in width and about 7 to 15 mm in length. In general it is preferable that the window of the enclosure be positioned within a distance of about 0.1 to 5.0 cm of the situs to be thermally stimulated, and more preferably about 0.4 to 1.0 of the situs. However, the distance can be modified in accordance to the particular situs and subject response to the stimulation so that a measurable withdrawn latency time period is obtained for placebo and drugs. This can be done without undue experimentation by a person of average skill in this art.

The intensity of the light beam may simply be regulated as determined by the distance to the situs of the subject at which the window through which the beam is emitted is placed.

Typically, measurable withdrawal latency time periods will fall between 1 and 60 seconds, more preferably between 1 and 30 seconds, and still more preferably between 1 and 15 seconds. However, the withdrawal latency time periods can be varied by controlling the distance of the light window to the subject situs, the intensity of the light beam, the dose of the drug, and the like.

In another particularly preferred embodiment for determining hyperalgesia in an experimental animal, the apparatus further comprises a light beam transparent base having a top surface upon which to deposit the experimental animal and a bottom surface in the vicinity of which is positioned said light beam generating means, and an enclosure capable of containing an experimental animal and permitting the inspecting of the events occurring therewithin by the human eye, the enclosure being positioned on the top surface of the base after depositing the animal thereon, whereby the base and the enclosure define the predetermined space within which the animal is unrestrained.

Typically, the light beam transparent base may be made of plastic, wire mesh or glass. However, any light transparent material may also be utilized in its construction.

The base is generally positioned horizontally so that the animal may remain unstressed on its top surface. Underneath the base enough space must be allowed for the insertion of the movable light beam generating means, and in the particular embodiment where it is contained in an enclosure along with the detecting means, starting means and stopping means enough room must be left for the entire enclosure to be positioned at a distance from the situs of the animal effective to attain a measurable withdrawal latency time period.

In general, the enclosure placed over the animal may be made of a plastic, glass or wire mesh, which optionally may be provided with ventilation holes.

The various methods are conducted with the apparatus of the invention by positioning the apparatus at an appropriate distance from the situs of the subject, connecting the apparatus to a power source and starting its operation. The latter is generally done manually since this permits the starting of the means for measuring time at a point in which the subject is unstressed and resting.

Typically, when the methods are practiced with a human subject, the human may be in a sitting, lying or standing position and the situs may be on the palm of the hand, the plant of the foot, the forearm and the like. However, other sites may also be utilized if appropriate.

In general, the situs of the human is positioned on a surface such as the light transparent base so that the incident light beam may be focused onto it.

When the present apparatus is utilized for measurements of the response of an experimental animal to thermal stimulation the animal is placed onto the base and an enclosure placed over it. The enclosure must be large enough so that the animal is not physically restrained from moving by the proximity of the walls of the container. Instead, the enclosure must be large enough so that the animal may relax and not feel threatened by its proximity.

After a period of time of about 1 second to 10 minutes, and more commonly about 1 to 5 minutes, the animal typically comes to a resting position, at which time the testing period may be started by operation of the starting means of the apparatus.

In one of the embodiments, the method of the invention is a high sensitivity in vivo method of discerning a peripherally-mediated response to thermal stimulation caused by a drug in an unrestrained subject, comprising (a) administering a drug to said subject for local delivery to a first situs thereof;

(b) exposing said situs to an amount of radiant heat effective to produce situs withdrawal after a latency time period in the absence of said drug;

(c) allowing said subject to spontaneously withdraw said situs from said radiant heat which is immediately discontinued;

(d) measuring the withdrawal latency time period elapsed between steps (b) and (c);

(e) administering a placebo to a second situs of said subject, said second situs being contralateral to said first situs and not being affected by said drug;

(f) repeating steps (b) through (d); and (g) subtracting said drug withdrawal latency time period from said placebo latency time, whereby if the difference is less than about 1 second the drug is said to act substantially like the placebo, if the difference is about 1 second or greater the drug is said to produce peripherally mediated hyperalgesia and if the difference is about −1 second or less the drug is said to produce peripherally-mediated hyperalgesia.

Typically, the drug may be administered by injection, e.g., subcutaneously, by making an incision in the tissue of an area which may locally deliver the drug to the desired situs, or other known methods. Typically, after a drug or placebo is administered there is a waiting period for the effect to be seen. This period varies and it is prudent to do a time course for a response to thermal stimulation by the subject for each particular composition administered prior to practicing the methods of the invention. For drugs such as morphine, carrageenan (CARRA), indomethacin, yeast, complete Freund's adjuvent and fentanyl the waiting period is about 1 to 4 hours. However, for other drugs, the period for eliciting a local response may be shorter or longer.

There are other means for producing a peripheral modification of the subject's response to the thermal stimulation which are encompassed by the present definition of temperture. One example is thermal injury produced by radiation, immersion in a heated environment or contact with a heated surface, among others. Another example is neuropathic damage which may be produced pharmaceutically or surgically.

The amount of radiant heat to which a subject situs is exposed produces typically a temperature at the situs of between about 28° and 47° C., and more preferably about 30° to 45° C.

The volume of the drug and/or placebo administered to the subject is preferably a small one, and typically about 0.01 to 0.4 ml and preferably about 0.01 to 0.5 ml in a physiological saline solution or other physiologically acceptable solutions which may bring the drug into suspension and/or solution.

In the case of an experimental animal the situs is typically the plantar surface of the paw, and more preferably of the hind paw since the animal tends to rest thereon. Typically, the time between the administration of a drug and the placebo for conducting this method is about 1 second to 10 minutes, and preferably between 5 seconds and 1 minute. Given the fact that the period for eliciting a response in the animal is several folds larger than the time between the administration of a drug and the placebo it is considered that the latter time is negligible.

The physiologic response to tissue damage is pain, swelling, hyperthermia, erythema and loss of function; signs which collectively comprise inflammation. Research on the mechanism of inflammatory pain (e.g., hyperalgesia) and drugs which block it has considerable clinical import. A major component of human pain and suffering is related to the hyperalgesia due to inflammation. For example, pain due to surgery, rheumatoid arthritis, osteoarthritis, acute trauma (e.g., car accidents, gunshot wounds) and some forms of cancer pain are all related to the process of inflammation. Despite a critical need for treating these forms of pain, the development and evaluation of new analgesic and anti-inflammatory drugs is limited by our ability to measure hyperalgesia in an inflamed area. A precise and sensitive method for measuring hyperalgesia promotes research on the mechanisms and treatment of inflammatory pain.

Preferably, the first and second situses of the experimental animal are located in two contralateral paws, and still more preferably in the plantar surfaces thereof.

In a preferred embodiment of the above method steps (a) and (e) are conducted prior to the remaining steps, thereby minimizing the difference in the latency period prior to the measurement step.

In another preferred embodiment of the above method steps (b) through (d) and (f) through (g) are conducted repeatedly at a preset time interval to obtain a time-response curve.

The interval may be of about 15 minutes to 100 hours, and preferably about 60 minutes to 120 minutes. However, the effect of the drug or placebo must still be present.

In another embodiment of the invention, after conducting a time-response curve for one dose of the drug, the above method further comprises repeatedly conducting steps (a) through (g) with different amounts of the drug when it is found that in step (g) the drug withdrawal latency time period is within less than one unit of the placebo withdrawal latency time period, thereby obtaining a drug-response curve.

In general, the values of the different doses of drug that may be administered to the subject vary with the drug. These values can be determined by an artisan without undue experimentation.

This invention also provides a high sensitivity in vivo method of determining the response to thermal stimulation caused by a drug in an unrestrained subject, which comprises (a) administering a placebo to said subject;

(b) exposing a predetermined situs of said subject to an amount of radiant heat effective to produce situs withdrawal after a latency time period;

(c) allowing for said subject to spontaneously withdraw the situs from the heat;

(d) measuring the withdrawal latency time period elapsed between steps (b) and (c);

(e) administering the drug to said subject;

(f) repeating steps (b) through (d); and (g) subtracting said drug withdrawal latency time period from said placebo withdrawal latency time period, whereby if the difference is less than about 1 second the drug is said to act substantially like the placebo, if the difference is about 1 second or greater the drug is said to produce hyperalgesia and if the difference is about −1 second or less the drug is said to produce hyperalgesia.

Each particular step of this method may be conducted under the same conditions as similar steps of the prior method. However, this is a more general method than the previous one since both the placebo and the drug may be administered systemically as well as locally to the subject. If subsequent to systemic administration of the drug it is determined that the drug causes, say, hyperalgesia to thermal stimulation but when both the drug and the placebo are locally administered there is no difference in the two responses to thermal stimulation it may be said that the drug acts centrally. On the contrary, if no difference is seen in the responses obtained by administering the drug and the placebo systemically but when both the drug and the placebo are administered peripherally there is a significant difference between the two responses to thermal stimulation it can reliably be stated that the drug acts peripherally.

In a particular embodiment of this method the placebo is administered for local delivery to a first predetermined situs of the subject prior to exposing it to the light beam and the drug is administered for local delivery to a second situs of the same subject which is contralateral to the first situs, and the difference obtained by subtracting the drug withdrawal latency time period from the placebo withdrawal latency time period is less than about 1 second the drug is said not to act peripherally.

Also provided herein is a high sensitivity in vivo method of discerning response to thermal stimulation caused by a second drug after the administration of a first hyperalgesic drug in an unrestrained subject, which comprises (a) administering a first drug to said subject for local delivery to a first situs thereof;

(b) exposing said situs to an amount of radiant heat effective to produce situs withdrawal after a latency time period in the absence of said first drug;

(c) allowing said subject to spontaneously withdraw said situs from said radiant heat which is immediately discontinued;

(d) measuring the withdrawal latency time period elapsed between steps (b) and (c);

(e) administering a placebo to a second situs of said subject, said second situs being contralateral to said first situs and not being affected by said first drug;

(f) repeating steps (b) through (d); and (g) subtracting said first drug withdrawal latency time period from said placebo latency time, whereby if the difference is less than about 1 second the first drug is said to act substantially like the placebo, if the difference is about 1 second or greater the first drug is said to produce peripherally mediated hyperalgesia, and if the difference is about −1 second or less the first drug is said to produce peripherally-mediated hyperalgesia.

(h) administering to said subject a second drug suspected of countering the hyperalgesic effect of the first drug;

(i) repeating step (f); and (J) subtracting said first drug withdrawal latency time period from said second drug withdrawal latency time period to obtain a first coefficient and subtracting said second drug withdrawal latency time period from said placebo withdrawal latency time period to obtain a second coefficient, whereby if the first coefficient is between about −1 and 1 it is said that the second drug fails to significantly change the effect of the first drug, if the first coefficient is about −1 or less the second drug is said to further enhance the hyperalgesic effect of the first drug, if the first coefficient is about 1 second or greater but less than about 1 sec of the second coefficient the second drug is said to cause hyperalgesia and if the first coefficient is greater than about the second coefficient the second drug is said to cause analgesia, and whereby if the second drug is administered for local delivery to the same situs as the first drug, the second drug is said to cause a peripherally mediated effect.

Also provided is a high sensitivity in vivo method of discerning a peripheral response to thermal stimulation in an unrestrained subject which comprises (a) exposing a first situs of said subject to an amount of radiant heat effective to produce situs withdrawal;

(b) allowing said subject to spontaneously withdraw said situs from said radiant heat which is immediately discontinued;

(c) measuring the withdrawal latency time period elapsed between steps (a) and (b);

(d) exposing a second situs of said subject to a similar amount of radiant heat used in step (a), said second situs being contralateral to said first situs;

(e) repeating steps (b) and (c); and (f) comparing said first situs withdrawal latency time period with said second situs withdrawal latency time period, whereby if the difference is less than about one second both situses are said to act equivalently and if the difference is about 1 second or greater the situs with the lower latency period is said to be afflicted with peripheral hyperalgesia with respect to the other side.

As in the case of the previous methods the different steps which are part of this method may be practiced as described above for the other methods.

The apparatus and the methods of the invention are particularly suited for application to the study of inflammation and/or damage stimulating behavioral responses to thermal stimulation.

Having now generally described this invention, the same will be better understood by reference to certain specific examples, which are included herein for purposes of illustration only and are not intended to be limiting of the invention or any embodiment thereof unless so specified.

EXAMPLE 1

Male Sprague-Dawley rats (Charles River Inc., 250–300 g) were maintained in an animal room (lights on 06.00–18.00 h) with water and food ad libitum for at least 1 week before testing. All studies employed randomized, complete block, vehicle-controlled designs with observers blind as to treatment allocation. Animals were tested once only at each time point. The IASP Ethical Guidelines were adhered to in these studies.

Initial studies determined the cutaneous temperature of the hind paw in 8 rats held on a glass floor during exposure to radiant heat. A thermocouple was placed under the heel of the hind paw. The plantar surface of one paw received a subcutaneous (s.c.) injection of 1.0 mg carrageenan (CARRA) in 0.1 ml saline, and the other paw was injected with the same volume of 0.9% saline (SAL). Both paws were tested 2 h after injection.

The averages of 3 trials were taken for each paw with 10 min between successive tests. The withdrawal latency and the cutaneous temperature at every second and at the time of withdrawal were recorded by a microprocessor.

To assess nociceptive responses to thermal stimuli, rats were placed in a clear plastic chamber (18 cm×29 cm×12.5 cm) with a glass floor and allowed to acclimate to their environment for 5 rain before testing. During this time, rats initially demonstrated exploratory behavior but subsequently stopped exploring and stood quietly with occasional bouts of grooming. After the acclimation period, the radiant heat source was positioned under the glass floor directly beneath the hind paw. A trial was commenced by a switch which activated the radiant heat source and started an electronic timer. The radiant heat source consisted of a high intensity projector lamp bulb (Osram 58-8007, 8 V, 50 W) located 40 mm below the glass floor and projecting through a 5 mm×10 mm aperture in the top of a movable case. A photoelectric cell aimed at the aperture detected light reflected from the paw and turned off the lamp and the electronic clock when paw movement interrupted the reflected light. At the same time, a tone was emitted. The withdrawal latency to the nearest 0.1 sec was determined using the electronic clock circuit and a microcomputer.

Three other response measures of behavioral hyperalgesia to thermal stimuli were taken: (1) the velocity of the withdrawal reflex (given an ordinal score of 0 if withdrawal movement was completed within 1 sec, or a score of 1 if the reflex persisted beyond 1 sec); (2) the presence or absence of licking; and (3) the duration of the hind paw withdrawal from the floor. The duration of the hind paw withdrawal was the time measured with a stopwatch from the beginning of the withdrawal movement, signaled by the tone, to the moment when the animal returned its paw to the glass floor.

The time course of these response measures to thermal stimuli was determined in 16 rats who received an s.c. injection of 1.0 mg CARRA into the plantar surface of one hind paw with no injection into the other paw. The behavioral profiles of both the CARRA and untreated, contralateral hind paws were obtained by periodically measuring paw withdrawal latency, paw withdrawal velocity, paw licking and the duration of paw withdrawal during a 96 h period.

To examine the possible contribution of repeated thermal stimulation on the development of CARRA-induced hyperalgesia, 5 different groups of rats (8/group) were tested only once at 1, 2.5, 4, 8 or 24 h after injection of 3 mg of CARRA. Another group of animals (n=8) were tested at baseline and at each of the selected time points. The 3 mg dose of CARRA was selected to provide a sustained period of hyperalgesia, during which 6 testing sessions with the thermal device were conducted.

The thermal device was compared to the Randall and Selitto mechanical device for detecting dose-related cutaneous hyperalgesia. Three different doses of CARRA, 0.5 mg, 1.0 mg or 2.0 mg, were used and compared to a SAL control with 8 rats/group. The drugs were injected s.c. into one hind paw with no injection into the other paw. Edema, temperature and hyperalgesia to both thermal and mechanical stimuli were assessed at baseline, and at 2.5, 4, 7 and 24 h after injection. Dorsal-plantar paw thickness, measured to 0.1 mm with a vernier caliper, was used as an index of edema. The temperature of the plantar surface of the paws was measured by a contact thermocouple placed under the heel. Paw edema and local hyperthermia were used to establish the time course and magnitude of dose-related CARRA-induced inflammation.

Nociceptive responses to mechanical stimuli were determined by the method of Randall and Selitto (12.Moskowitz, R. et al, Generation of kinin-like agents by chondroitin sulfate, heparin, chitin sulfate and articular cartilage: possible pathophysiolog implications. J Lab Clin Med (1970); 76:790–8). The apparatus employed a pneumatic system connected to the graphite coated plunger of a 5 ml glass syringe. The plunger of this syringe transmitted the mechanical force by a lever to an acrylic cone (36° slope, rounded tip with a 1.2 mm radius). These dimensions match a common commercial version of the Randall and Selitto device (Ugo Basille Analgesy-meter, D. Clark, pers. commun., Coburn Inst., Lehigh Valley, Pa.). The exerted force increased at a constant rate of 25.5 g/sec. The nociceptive threshold, expressed in grams, was that force applied to the dorsal surface of the rat hind paw which caused each animal to withdraw the paw. The cut-off was 300 g. The sequence of testing animals on the thermal and mechanical devices was counterbalanced such that half of each group was tested first on the thermal and second on the mechanical device; the order was reversed for the remaining rats.

The ability of the thermal and mechanical methods to detect the blockade of CARRA-induced hyperalgesia by analgesic drugs was assessed and compared in rats pretreated with either morphine sulfate 3 mg/kg (MS) or indomethacin 2 mg/kg (INDO). Four groups of 10 rats were used. The groups received 3 injections as seen in Table 3. These 4 groups will be referred to as SAL/SAL, CARRA/SAL, CARRA/INDO and CARRA/MS. The times of d rug injection were selected to permit concurrent development of peak analgesic effects of MS and INDO. Behavioral responses to thermal and mechanical stimuli were measured for both the CARRA- and contralateral untreated hind paws at baseline, and at 2 and 3.5 h after the first injection.

TABLE 3

DRUG SCHEDULE FOR THE INDOMETHACIN AND MORPHINE STUDY

| Group | Time zero Hind paw* s.c. | i.p. | 60 min i.p. |
|---|---|---|---|
| 1 | SAL | SAL | SAL |
| 2 | CARRA | SAL | SAL |
| 3 | CARRA | INDO | SAL |
| 4 | CARRA | SAL | MS |

*The contralateral hind paw was untreated.

Statistical analysis was carried out using the analysis of variance (ANOVA) for repeated measured for overall effects, with Duncan's new multiple range test for comparison between groups (Winer, B., Statistical Principles in Experimental Design, McGraw-Hill, New York, (1975)). Student's t test was also used when appropriate. Dose-response relationships at the time of peak effects were analyzed by linear regression with ANOVA testing the zero slope hypotheses (Winer, supra). Statistical significance was taken at $P<0.05$. Values are quoted in the text as means±S.E.M.

In all studies, except where noted, 1.0 mg of lambda CARRA (Sigma Chemical Co., C-3889) in 0.9% sterile saline was suspended by sonication and injected s.c. into the plantar surface of a hind paw with a 25-gauge needle. INDO (Merck, Sharp and Dohme Co., West Point, Pa.) was dissolved in 0.1% (w/v) sodium carbonate. Morphine sulfate was dissolved in 0.5% saline. The s.c. hind paw injection volume was 0.1 ml while the i.p. injection volume was 0.1 ml/100 g body weight.

RESULTS

The cutaneous temperatures of both CARRA-and saline-treated paws increased during exposure to radiant heat (data not shown). As compared to the saline-injected paws, the CARRA-injected paws had significantly greater initial paw temperatures (30.5°±0.2° C. vs. 27.9°±0.2° C.; $P<0.001$). In addition, the CARRA-treated paws exhibited shorter withdrawal latencies as compared to saline-treated paws (3.5±0.6 sec vs. 10.9±0.6 sec.; $P<0.001$). The significantly shorter latencies of CARRA-treated paws correspond to lower nociceptive threshold temperatures (38.5°±0.7° C. vs. 45.2±0.2° C.; $P<0.001$).

To determine that the time course of hyperalgesia following administration of CARRA was not influenced by repeated testing, we compared rats tested at 6 time points to several groups of rats each tested only once (Table 3). While the withdrawal latencies of the saline-treated paws and the contralateral (untreated) paws of all groups remained near baseline values throughout the testing session, the CARRA-injected paws exhibited significantly shorter latencies from 1 through 24 h following injection (Table 4 below).

latencies to thermal stimulation with an onset by 1 h and a peak at the 2.5 h time point as compared to saline-treated animals. The magnitude of the decrease in withdrawal latency was significantly dose related (slope=−3.26; $F(1,30)=36.58$; $P<0.001$). The paw withdrawal exhibited a dose-related peak in its duration at 2.5 h following injection of CARRA (slope=7.37; $F(1,30)=13.71$; $P<0.01$). Both contralateral untreated paws and saline-treated paws exhibited stable values of paw withdrawal latency and duration of paw withdrawal throughout the testing period.

The time course of edema and local hyperthermia after s.c. injection of saline or 0.5, 1.0 and 2.0 mg CARRA is presented in FIG. 5. CARRA-induced inflammation resulted in significant edema $F(35,280)=39.78$; $P<0.001$) over time. There was a significant dose-response relationship (slope=1.09; $F(1,30)=96.83$; $P<0.001$) between CARRA and edema. The edema was significantly greater ($P<0.01$) for the 3 doses of CARRA than that observed in the SAL group as early as 1 h. The peak was reached between 2.5 and 4 h after injection of each dose. Edema was still present 24 h after the injection of 1. 0 and 2.0 mg CARRA ($P<0.01$). The 2 mg CARRA group was significantly different from all the other groups at the 2.5, 4 and 7 h time points. Contralateral edema was not observed. Paw temperature followed a parallel time course $F(35,280)=6.11$; $P<0.001$). The local hyperthermia response was linearly related to the dose of CARRA (slope=1.30; $F(1,30)=84.45$; $P<0.001$). The

TABLE 4

THE EFFECT OF REPEATED TESTING ON PAW WITHDRAWAL LATENCY*
IN CARRAGEENAN-INDUCED HYPERALGESIA

| | h | Baseline | 1 h | 2.5 h | 4 h | 8 h | 24 h |
|---|---|---|---|---|---|---|---|
| Same group tested at each time point | | | | | | | |
| (1) Saline-injected paw | 8 | 9.8 ± 0.3 | 11.4 ± 0.4 | 10.7 ± 0.5 | 9.6 ± 0.6 | 9.2 ± 0.6 | 9.8 ± 0.2 |
| Contralateral uninjected paw | | 9.6 ± 0.4 | 10.0 ± 0.5 | 9.6 ± 0.5 | 9.0 ± 0.5 | 9.7 ± 0.4 | 9.4 ± 0.5 |
| (2) Carrageenan-injected paw** | 8 | 9.7 ± 0.3 | 3.7 ± 0.6*** | 2.0 ± 0.2*** | 1.8 ± 0.1*** | 2.5 ± 0.2*** | 6.5 ± 0.5*** |
| Contralateral uninjected paw | | 10.0 ± 0.4 | 9.6 ± 0.3 | 9.8 ± 0.4 | 9.8 ± 0.4 | 9.0 ± 0.4 | 10.1 ± 0.3 |
| Different groups tested only at 1 time point | | | | | | | |
| (3) Carrageenan-injected paw | 40 (8/observation | | 4.6 ± 0.05*** | 1.8 ± 0.3*** | 1.8 ± 0.01 | 2.8 ± 0.4*** | 5.8 ± 0.8*** |
| Contralateral uninjected paw | | | 10.7 ± 0.5 | 8.9 ± 0.8 | 9.9 ± 0.6 | 9.1 ± 0.4 | 9.1 ± 0.5 |

*Mean ± S.E.M. (sec).
**Rat hind paws were injected with either 3 mg carrageenan or saline at time zero.
***Significantly different ($P < 0.01$) from saline paw and contralateral paw.

The time course of the paw withdrawal latencies did not differ between the CARRA group tested at all time points and the separate CARRA groups tested at only one time point each.

The time course of several behavioral correlates of CARRA-induced hyperalgesia was next determined. The paw withdrawal latency decreased significantly ($P<0.001$) by 1 h after CARRA injection, to reach its minimal value at 2.5 h. At 4 h, the paw withdrawal latency started increasing, and hyperalgesia was not detected at 8 h. With the onset of hyperalgesia, the withdrawal movement of the CARRA-treated paw became slow, the animal did not lick its paw and the paw was held above the glass floor for a longer period of time. Interestingly, these behavioral correlates of hyperalgesia were detected long after the paw withdrawal latency had returned to normal.

The thermal device was next evaluated for detecting dose-related inflammation produced by 0.5, 1.0 or 2.0 mg of CARRA. CARRA-treated rats exhibited significantly shorter ($F(35,280)=6.33$; $P<0.001$) withdrawal onset in local hyperthermia was reached at 1 h, while the peak was between 2.5 and 4 h after injection of CARRA.

Administration of CARRA also resulted in hyperalgesia to mechanical stimuli $F(35,280)=2.93$; $P<0.01$). CARRA-induced hyperalgesia was not detectable until 2.5 h after injection (FIG. 6). Dose-related changes in withdrawal pressure were observed in response to mechanical stimuli (slope=−1.19; $F(1,30)=20.08$; $P<0.001$). Contralateral untreated paws did not exhibit significant differences from saline-treated paws.

The ability of the thermal and mechanical devices to detect blockade of CARRA-induced hyperalgesia was evaluated by injecting (ip) either indomethacin (2 mg/kg) or morphine (3 mg/kg). ANOVA revealed a significant drug effect when using radian heat as the noxious stimulus $F(6,72)=8.80$; $P<0.01$). In the CARRA/SAL group the CARRA-injected paws exhibited significantly ($P<0.01$) shorter paw withdrawal latencies as compared to contralateral (untreated) paws at 2 and 3.5 h following injections. Conversely, withdrawal latencies of the CARRA-treated paws of both the indomethacin and morphine groups did not differ from latencies of their contralateral untreated paws or latencies observed in the SAL/SAL control group.

When tested with the Randall-Selitto mechanical device, the inflamed paws of the CARRA/SAL group exhibited significantly lower withdrawal pressures as compared to their contralateral untreated paws. ANOVA indicated a significant drug effect for mechanical testing $F(6,72)=4.01$; $P<0.01$). The CARRA-induced hyperalgesia to mechanical stimuli was not observed in rats treated with either indomethacin or morphine sulfate.

The results of these studies indicate that the thermal method provides a quantitative measurement of the behavioral correlates of hyperalgesia. Initial studies demonstrate that the decreased paw withdrawal latency corresponds to the decreased nociceptive threshold observed during the course of hyperalgesia. Repeated testing does not alter the paw withdrawal latencies of either inflamed or untreated paws. Several other response measures determined by this method had a prolonged time course to hyperalgesia as compared to changes in paw withdrawal latency. Both the thermal method and the Randall-Selitto method detect dose related CARRA hyperalgesia and its blockade by a prototype non-steroidal anti-inflammatory (INDO) and opiate (MS) analgesic.

Although CARRA-induced inflammation was first described in 1962 (Winter et al, Carrageenan-induced edema in hind paw of the rat as an assay for antiinflammatory drugs, Proc. Soc. exp. Biol. Med., 111: 544–547 (1962)) and has since been employed widely as an animal model to screen for clinically useful non-steroidal anti-inflammatory drugs (Otterness et al, Laboratory models for testing nonsteroidal anti-inflammatory drugs, in Nonsteroidal Anti-inflammatory Drugs, Lombardino, J., ed., Wiley, New York, pp. 112–252 (1985)), most studies have utilized edema as the dependent measure. Comparatively little is known about CARRA-induced hyperalgesia (Vinegar et al, Antagonism of pain and hyperalgesia. In: J. R. Vane and S. M. Ferreira (Eds.), Handbook of Experimental Pharmacology, Inflammation, 50/1, Springer, Berlin, pp. 209–222 (1978)). The present findings indicate that administration of 1 mg of CARRA results in the production of a cutaneous hyperalgesia to thermal stimuli, as indicated by a decreased withdrawal latency, which begins by 1 h, peaks at 2–3 h and subsides by 8 h following injection.

The withdrawal latencies of saline-injected paws occurred at a nociceptive threshold temperature of $45.2°\pm0.2°$ C. This finding is in agreement with the thermal nociceptive threshold observed in humans, monkeys, guinea pigs and rats (Dubher et al, Responses of facial cutaneous thermosensitive and mechanosensitive afferent fibers in the monkey to noxious heat stimulation, Adv. Neurol., 4: 61–71 (1974); Hardy et al, Threshold of pain and reflex contraction as related to noxious stimulation, J. Appl. Physiol., 5(1953) 725–739; Willis, W. D., The Pain System, Karger, Basel (1985)). Following CARRA inflammation, the paw withdrawal occurs at a threshold temperature of $38.5°\pm0.7°$ C. The CARRA-induced decrease in the paw withdrawal latency corresponds to the decrease in the thermal nociceptive threshold. For these reasons, the paw withdrawal latency is considered to be an index of the thermal nociceptive threshold.

Since a CARRA-treated paw exhibits both erythema and hyperthermia, it is possible that the inflamed paw absorbs radiant heat more effectively and requires a smaller temperature change to reach the $38.5°$ C. threshold temperature as compared to a saline-treated paw. Therefore, we examined whether these factors contribute to the decreased paw withdrawal latency observed after CARRA. Comparison of time response curves indicates that inflamed paws reach the $38.5°$ C. nociceptive threshold approximately 0.6 sec sooner than the saline-treated paws. This finding indicates that the difference in withdrawal latencies between the inflamed and saline-treated paws (i.e., approximately 6–8 sec) is predominately due to hyperalgesia and that local erythema and hyperthermia contribute very little to the observed difference.

We ruled out any effect of repeated heating of the paw on the development of CARRA hyperalgesia. Although heat is known to sensitize C polymodal fibers (Beitel et al, Sensitization and depression of C-polymodal nociceptors by noxious heat applied to the monkey's face, in Advances in Pain Research and Therapy, Vol. 1, J. J. Bonica and D. Albe-Fessard (Eds.), Raven Press, New York, pp. 149–153 (1976)); Dubner et al, supra), we failed to detect any effect of repeated testing on behavioral hyperalgesia (Table 4 above). This is probably due to the fact that the rats were tested only once at each testing session, and that the smallest time interval between tests was 1 h. Furthermore, since the animal was allowed to freely escape from the stimulus, it is likely that the cutaneous temperature never exceeded the thermal nociceptive threshold for a sufficient amount of time to allow sensitization to occur (Beitel et al, supra; Dubner et al, supra). The stability of thee control values (i.e., saline and untreated contralateral paws) in the time course experiment constitutes a second argument against a contribution of repeated testing and indicates that the observed hyperalgesia was due to CARRA.

Since the thermal method uses unrestrained animals, several behavioral responses to cutaneous hyperalgesia can be measured. The normal paw withdrawal occurs after a 9–10 sec latency and is characterized as a quick movement, generally followed by licking the tested paw. The paw is returned to the glass floor within a few seconds. This behavioral profile changes with the onset of hyperalgesia. The CARRA-treated paw is withdrawn at significantly shorter latencies following exposure to radiant heat and the withdrawal is a slow movement, the paw is not licked and it remains elevated from the glass floor for an extended duration. Although changes in all response measures peaked at 2.5 h after CARRA injection, the velocity of withdrawal, paw lick and duration of withdrawal can be distinguished from paw withdrawal latency by their prolonged time course. Significant alterations in these 3 response measures can be demonstrated up to 48 h after a single injection of CARRA, while paw withdrawal latency returns to near-baseline values after 8 h. The differences in the time course of these response measures suggest that they represent complex behaviors resulting from sensory integration from input at different site in the CNS. In addition, these findings emphasize the value of a multidimensional measurement of behavioral responses to noxious stimuli.

Increases in the duration of flexion reflexes have been noted also in neurophysiologic investigations of hyperalgesia. Beitel et al, supra reported the occurrence of afterdischarge in sensitized polymodal nociceptors following heat stimuli. Woolf, C. F., Evidence for a central component of post-injury pain hypersensitivity, Nature (Lond.), 306: 686–688 (1983)) observed a sustained flexion after injury and correlated this behavior with an increase of the afterdischarge in the flexor efferent motor nerve evoked by both thermal and mechanical stimuli. The increased duration of paw withdrawal observed in this study could then be due to either a prolonged afferent discharge or efferent drive.

Comparison of the thermal to the mechanical method indicates that both devices can measure dose-related hyperalgesia and the blockade of hyperalgesia by either morphine or indomethacin. However, the two methods differ in their sensitivity even when testing the same group of animals on both devices. At 1 h after CARRA injection hyperalgesia was not detectable with the mechanical device. In contrast, a robust hyperalgesia was present in the same groups when testing with thermal stimuli. Since significant changes in edema and hyperthermia were also observed at 1 h, the differences in the mechanical and thermal methods appear to be due to a difference in bioassay sensitivity.

Two lines of statistical data provide further support for a difference in bioassay sensitivity between the two methods. First, comparison of the results from the thermal and mechanical devices indicates that the thermal device provides a greater signal-to-noise ratio. This ratio is indicated by larger F ratios following ANOVA (i.e., the ratio of the mean square of the treatment effect to the mean square of the error). For the comparative studies presented in this paper (CARRA dose-response and MS/INDO blockade), the ANOVA F ratios for the thermal device were more than double those F ratios generated from data collected with the mechanical device. In more than 9 months of study, we have consistently observed F ratios from the thermal device to be on the average nearly 2-fold greater than F ratios gathered from the mechanical device. Thus, the thermal device provides data with greater statistical power as compared to the Randall-Selitto mechanical device.

The second line of evidence comes from comparison of the slopes of the dose-response curves. To allow a direct comparison of the ability of the two methods to measure behavioral hyperalgesia, data from the thermal and mechanical devices were normalized by dividing observations taken at 2.5 h by baseline values. As described earlier, both methods detect dose-related hyperalgesia. Further analysis reveals that the dose-response slope of the thermal method is more than 2.6-fold steeper than the slope derived from the mechanical method; these slopes differ significantly ($F(2,43)=5.38$; $P<0.01$). These findings indicate that the thermal method has a greater bioassay sensitivity for detecting behavioral hyperalgesia, as evidenced by a given dose of CARRA producing a larger departure from baseline measures.

The greater bioassay sensitivity of the thermal device may be due in part to differences in methodology. The thermal device tests an unrestrained rat exposed to minimal environmental cues which precede or signal the commencement of a testing session. In contrast, the Randall-Selitto mechanical device requires a forcibly restrained rat. The mechanical method may then facilitate a learning effect (Vinegar et al, supra), in which paw withdrawal occurs at a force below the nociceptive threshold. An additional factor is immobilization, which activates stress-related systems such as the pituitary-adrenal and sympatho-adrenomedullary axes (Mueller, G., Beta-endorphin immunoreactivity in rat plasma: variations in response to different physical stimuli, Life Sci., 29: 1669–1674 (1981)); Sourxes, T., Pathways of stress in the CNS, Proge. Neuropsychopharmacol. Biol. Psychiat., 7: 389–411 (1983)). The amount of immobilization used in the Randall-Selitto method is stressful, as indicated both by behavioral struggling and by higher levels of blood-borne immunoreactive beta-endorphin (Hargreaves and Joris, unpublished observations). Both a learning effect and stress may diminish the sensitivity of the Randall-Selitto method.

An additional factor contributing to bioassay sensitivity may be the development of hyperalgesia which differs in responsiveness to thermal and mechanical stimuli. Supporting this point, Handwerker et al, Nociceptor functions in the intact skin and in neurogenic or non-neurogenic inflammation, Acta physiol. hung., in press. recorded C polymodal nociceptors in CARRA-inflamed paws after thermal and mechanical stimulation. Their findings indicate that CARRA pretreatment alters C-fiber responsiveness to thermal stimuli more strongly than to mechanical stimulation. In addition, Benoist et al, (Benoist et al, Changes in responses of ventrobasal thalamic neurons during carrageenan-induced inflammation in the rat, in Advances in Pain Research and Therapy, Vol. 9, Raven Press, H. L. Fields, F. Cervero and R. Dubner (Eds.), New York, pp. 295–303 (1985)), recorded from nociceptive neurons in the ventrobasal thalamus following injection of CARRA into the hind paw. They observed that administration of CARRA decreased the thermal threshold of these neurons and increased their responsiveness to thermal stimulation. In contrast there were no significant alterations in response to mechanical stimuli.

The experiments described herein validate the thermal device as an appropriate and sensitive method to quantify hyperalgesia. This new method represents a useful tool in the assessment of behavioral hyperalgesia.

EXAMPLE 2

Male Sprague Dawley rats (Charles River, Inc.; weight, 250–300 g) were maintained in an animal room (lights on 6 AM to 6 PM) with water and food ad libitum for at least 1 week before testing. All studies employed randomized vehicle-controlled designs with observers unaware of treatment allocation.

Hyperalgesia was determined using thermal stimulation. Unrestrained rats were placed within a transparent plastic chamber with a glass floor. After a 5-minute habituation period, the plantar surface of their paws was exposed to a beam of radiant heat. Paw withdrawal latency (PWL) was taken as an index of nociceptive threshold. Previous studies have demonstrated that organized intentional behaviors from which pain and analgesia can be inferred are correlated with withdrawal latency in this method (Hargreaves et al, A new and sensitive method for measuring thermal nociception in cutaneous hyperalgesia. Pain 32:77–88 (1988)).

In a first study, the peripheral effect of the $\mu$-agonist fentanyl (FEN) (Janssen Pharmaceutica) was assessed. One group (n=7) received initial injections (0.1 ml) of saline (SAL) into the plantar surface of both hind paws at time 0, and 90 minutes later received injections of SAL into both paws and subcutaneously (SC) into the neck. Three other groups (n=7–10) received initial injections (0.1 ml) of 2 mg of $\lambda$-CARRA (Sigma Chemical Co., C-3889) into both paws. Ninety minutes later, one CARRA group received an injection of 0.3 μg FEN into one inflamed paw, while SAL was injected into the other inflamed paw and injected SC into the neck. At the same time, another CARRA group received SAL injections into both paws and the same dose of FEN (0.3 μg) injected into the neck. The last CARRA group received SAL injections in both paws and in the neck. Rats were tested once at baseline and 2,3, and 4 hours after the initial paw injections.

The same experimental design was used to evaluate the peripheral analgesic effect of 10 μg of ethylketocyclazocine (EKC) (Sterling Winthrop Res. Inst.), a k-opiate agonist, instead of FEN.

In the last experiment, the dose-response relation and the stereoselectivity of the peripheral opiate effect were determined using another μ-agonist, levorphanol (Hoffmann-LaRoche Inc.), and its inactive dextrorotatory isomer, dextrophan (Hoffmann-LaRoche Inc.). Carrageenan (n=6) was injected into both paws and 90 minutes later SAL was injected into one hind paw, while the other inflamed paw was injected with either levorphanol (20, 40, 80, or 160 μg) or dextrophan (160 μg). Rats were tested once at baseline and 2,3, and 4 hours after the CARRA injections.

Statistical analysis was carried out using analysis of variance (ANOVA) for repeated measures for overall effect, with Duncan's multiple range test for comparison between groups (Winer, supra). To determine a dose-response relation for levorphanol, a linear regression ANOVA tested the zero slope hypothesis (Winer, supra). values are quoted in the text as means±SEM. In the first two studies, three of the four groups had the same drugs administered into both hind paws. For each of these groups, the mean latencies of both paws were used to determine the group mean. In the remaining group, which received a hind paw injection of opiate, each paw was analyzed separately, because one paw received the CARRA-opiate combination, whereas the other paw was injected with CARRA and SAL.

In the FEN experiment, the injection of CARRA into both paws followed by SAL resulted in a profound decrease in PWL (P<0.01) as compared to the control group receiving SAL for all injections. In rats injected with CARRA followed by opiate into one paw, the inflamed paws injected with 0.3 [204 g FEN were significantly less hyperalgesic (F[1,9]=27.25; P<0.001) than were the contralateral inflamed paws injected with SAL. This peripheral analgesic effect persisted for more than 2 hours. In contrast, the same dose of FEN had no effect when administered SC into a distant site in the neck.

Administration of CARRA into both paws followed by SAL injections resulted in sustained hyperalgesia (P<0.01) as compared to rats administered SAL only. In the group receiving CARRA followed by a peripheral opiate injection into on paw, 10 μg EKC produced a significant peripheral analgesia (F[1,8]=13.6; P<0.01) compared with contralateral inflamed paws injected with SAL. This effect persisted for more than 2 hours. In contrast, EKC had no effect when systemically administered.

Administration of levorphanol into an inflamed paw produced a peripheral dose-related analgesia (F[1,20]=11.9;P<0.005) as compared with the inflamed contralateral paw injected with SAL. The analgesic effect was most clearly evident with the 40[204 g (P<0.05), 80 g (P<0.01), and 160 g (P<0.01) doses. This peripheral analgesic effect was stereoselective, because administration of 160 μg of dextrorphan did not alter the nociceptive threshold. Levorphanol at these doses had no systemic effect because the contralateral saline-injected paws exhibited neither a significant difference between any groups nor a dose-response relation.

These results demonstrate that local administration of an opiate into an inflamed paw produces a dose-related analgesia restricted to the inflamed paw. These effects are opioid receptor-specific because levorphanol is analgesic, whereas its dextrorotatory isomer, dextrorphan, is inactive when administered into the inflamed paw. An additional test to determine opioid specificity, naloxone challenge, was avoided because of its reported agonist-like effects in this model of inflammation (Rios et al, Local inhibition of inflammatory pain by naloxone and its N-methyl quaternary analog. Eur J Pharmacol; 96:277-83 (1983).

If opiates were to act only in the central nervous system to produce analgesia, then a bilateral analgesic effect should have been observed in both inflamed hind paws, regardless of the site of administration. However, systemic administration of these low doses of FEN and EKC subcutaneously into the neck had no effect, whereas peripheral administration into an inflamed paw produced localized analgesia. Additional evidence for lack of a systemic opiate effect is the similar latencies for the SAL-injected contralateral paws of the group receiving local opiate and for the CARRA group receiving no opiate. Finally, the latencies of the SAL-treated paws of the four levorphanol groups were statistically indistinguishable, despite the dose-related analgesia observed in the opiate-treated paws. We interpret these results to indicate that opiate-induced analgesia is due to a peripheral mechanism as well as to its well recognized central mechanism of action. The peripheral analgesic effect is observed with both μ- and κ-agonists.

These results raise the question of the mechanism of this peripheral opiate effect. The two most likely targets are peripheral terminals of primary afferents and leukocytes, both of which are known to possess opioid receptors (Fields et al, Multiple opiate receptor site on primary afferent fibers, Nature; 284:351-3 (1980); Young et al, Opioid receptors undergo axonal flow. Science; 210:76-8 (1980); Teschemacher et al, Opioid peptides: do they have immunological significance?. Trends Pharmacol Sci; 6:368-70 (1985); Wybran, Enkephalins and endorphins as modifiers of the immune system: present and future. Fed Proc; 44:92-4 (1985)). An opioid effect on the nerve terminals may be direct, by modulating nociceptive transmission (Jurna et al, The effect of morphine on mammalian nerve fibers. Eur J Pharmacol; 44:339-48 (1977) and Frank et al, Effect of enkephalin, applied intracellularly, on action potentials in vertebrate A and C nerve fiber axons. Neuropharmacol; 26:61-6 (1987), or it may be indirect, by an antiinflammatory effect (Teschemacher et al, supra; Wybran, supra; Bartho et al, Opiate agonists inhibit neurogenic plasma extravasation in the rat. Eur J Pharmacol; 73:101-4 (1981); and Lembeck et al, Inhibition of neurogenic vasodilatation and plasma extravasation by substance P antagonists, somatostatin and (D-Met[2], Pro[5]-)enkephalinamide. Eur J Pharmacol; 85:171-6 (1982)).

Although opioid receptor binding sites have been detected in peripheral nerve trunks (Fields et al, supra and Young et al, supra), the effects of opiates administered perineurally have been equivocal. Morphine alters the compound action potential in some studies (Jurna et al, supra; Frank et al, supra), whereas others have either not observed this effect (Yuge et al, Direct opioid application to peripheral nerves does not alter compound action potentials. Anesth Analg; 64:667-71 (1985) or ascribed it to the presence of drug preservatives (Senami et al, Lack of opiate effects on cat C polymodal nociceptive fibers, Pain; 27:81-90 (1986)). In addition, perineural administration of opiates reduces patient report of pain in some (Mays et al, Pain relief after peripheral perineural injection of morphine, Pain; 1(suppl): S120 (1981) and Mays et al, Local analgesia without anesthesia using peripheral perineural morphine injections, Anesth Anlg; 66:417-20 (1987), but not all studies (Bullingham et al, Perineural injection of morphine fails to relieve postoperative pain in humans, Anesth Analg; 62:164-7 (1983).

Our finding that preservative-free opiates consistently produce analgesia when administered into inflamed peripheral tissue suggests that this may be a more accurate method for evaluating peripheral analgesic actions of opiates than is perineural administration. This proposition is supported by the fact that opioid receptors may be more highly concentrated in the nerve terminal, due to a preponderance of peripherally directed axonal transport (Fields et al, supra; Laduron, P. Axonal transport of opiate receptors in the capsaicin sensitive neurones, Brain Res; 294:157-60 (1984) and to the fact that these peripheral opioid receptors are functionally active under conditions of inflammation. In addition, opiate receptors located on non-neural elements (e.g., leukocytes) may participate in the modulation of peripheral inflammation and accompanying pain.

In addition, the present findings have potential therapeutic implications. Several undesirable side effects of opiates result from their actions in the CNS. When injected peripherally in inflamed tissue, small doses devoid of central effects may provide prolonged analgesia restricted to this area. Furthermore, the development of quaternary opiates that would not cross the blood-brain barrier and therefore activate only peripheral opioid receptors might lead to analgesic drugs lacking centrally mediated side effects of the opiates (Ferreira et al, Is methylnalorphinium the prototype of an ideal peripheral analgesic?, Eur J Pharmacol; 99:23-9 (1984), Smith et al, Peripheral anti-nociceptive effects of N-methyl morphine, Life Sci; 31:1205-8 (1982)). Such drugs would be of potential clinical utility in the management of analgesia and anesthesia.

The participation of a peripheral mechanism in opiate analgesia may provide a potential target for circulating opioid peptides such as pituitary beta-endorphin. For example, administration of corticotropin releasing factor increases circulating beta-endorphin and decreases postoperative pain (Hargreaves et al, Corticotropin releasing factor (CRF) produces analgesia in humans and rats. Brain Res; 422:154-7 (1987)), whereas suppression of beta-endorphin levels by administration of low levels of dexamethasone increases postoperative pain (Hargreaves et al, Dexamethasone alters plasma levels of beta endorphin and post-operative pain, Clin Pharm Ther, 42:601-607 (1987). Results from the present study suggest that one potential target for these circulating opioids is the peripheral modulation of nociception.

In conclusion, we have demonstrated that peripheral administration of opiates in the site of acute inflammation produces analgesia. This effect is peripherally mediated, opioid-specific and dose related. Peripheral terminals of primary afferents and leukocytes represent the most likely targets for this effect. These findings may have therapeutic implications through the use of a new route for the delivery of opiates or by the development of quaternary opiates with the potential to avoid centrally mediated side effects.

EXAMPLE 3

For evaluating the peripheral analgesic effects of opiates, rats were placed beneath an inverted clear plastic chamber on a glass floor. After a 5-min habituation period, the plantar surface of their paws was exposed to radiant heat; paw-withdrawal latency (PWL) was taken as an index of the nociceptive threshold. Previous studies have demonstrated that organized intentional behaviors from which pain and analgesia can be inferred are correlated with withdrawal latency in this model (Hargreaves et al, supra).

In an initial study, the peripheral effect of the kappa agonist EKC (Sterling Winthrop Res. Inst., N.Y.) was assessed. One group (n=7) received initial (injections (0.1 ml) of saline (SAL) into the plantar surface of both hind paws at time 0, and 90 min later received injections of SAL into both paws and subcutaneously (s.c.) into the neck. Three other groups (n=7-10) received initial injections (0.1 ml) of 2 mg of lambda CARRA into both paws. Ninety minutes later, one CARRA group received an injection of 10 $\mu$g EKC into one inflamed paw; SAL was injected into the other inflamed paw and also s.c. into the neck. At the same time, another CARRA group received SAL injections into both paws and the same dose of EKC (10 $\mu$g) injected s.c. into the neck. The last CARRA group received injections in both paws and the neck. Rats were tested once at baseline and 2, 3 and 4 h after the initial paw injections.

In the next experiment, the dose-response relationship and the stereoselectivity of the peripheral opiate effect were determined using a mu agonist, levorphanol (Hoffman-LaRoche Inc., N.J.) and its inactive dextrorotatory isomer, dextrorphan (Hoffman-LaRoche Inc., N.J.). CARRA (n=6) was injected into both paws and 90 min later SAL was injected into one hind paw, while the other inflamed paw was injected with either levorphanol (20, 40, 80 or 160 $\mu$g) or dextrorphan (160 $\mu$g). Rats were tested once at baseline and at 2 h after the CARRA injections.

For evaluating the effect of morphine on plasma extravasation, male Sprague-Dawley rats had catheters implanted in the left jugular vein under pentobarbital anesthesia. Two days after surgery, one hindpaw was injected s.c. in the plantar surface with 2 mg (in 0.1 ml saline) of lambda CARRA (Sigma Co., St. Louis), while the other hindpaw received 0.1 ml of saline. Ninety minutes later, rats were injected i.v. with either 2 mg/kg morphine sulfate (n=12) or saline (n=11); 15 min later, all animals received an i.v. injection of Evans blue dye (33 mg/kg). Dorsal-plantar paw thickness was measured to the nearest 0.1 mm at 120 min using a caliper. Edema was calculated by measuring the difference between the thickness of the control saline-injected paws and the thickness of the carrageenan-injected paws. The animals were then killed and a 6-mm punch biopsy of hindpaw skin (Baker Cummins, Fla.) was taken. The punch was positioned just proximal to the two distal callous pads on the plantar surface of the hind paws. Since Evans blue binds to plasma proteins normally restricted to the vascular compartment, its presence in s.c. tissue is a standard marker for plasma extravasation (Lembeck et al, Substance P as a neurogenic mediator of antidromic vasodilation and neurogenic plasma extravasation. Arch. Pharmacol., 310:175-183 (1979)). The dye was extracted from the tissue samples for 3 days by the addition of 2 ml of formamide. The optical density (620 nm) of the samples was converted to μg of dye by comparison of a standard curve of Evans blue dye in formamide.

For all studies, data were collected by an observer unaware of treatment allocation and analyzed by analysis of variance (ANOVA) for repeated measures followed by Duncan's multiple range test (Winer, supra). To determine a dose-response relationship for levorphanol-treated paws, a linear regression ANOVA tested the zero-slope hypothesis (Winer, supra).

Adminstration of CARRA into both paws followed by SAL injections resulted in a sustained hyperalgesia ($P<0.01$) as compared to rats administered SAL only. In the group receiving CARRA followed by a peripheral opiate injection into one paw, 10 μg of EKC produced a significant peripheral analgesia ($F[1,9]=13.6; P<0.01$) as compared to contralateral inflamed paws injected with SAL. This effect persisted for more than 2 h. In contrast, EKC had no effect when administered systemically.

Administration of levorphanol into an inflamed paw produced a peripheral, dose-related analgesia ($F[1,20]=11.9; P<0.005$) as compared to the inflamed contralateral paw injected with SAL. The analgesic effect was most clearly evident with the 40 μg ($P<0.05$), 80 μg ($P<0.01$) and 160 μg ($P<0.01$) doses. This peripheral analgesic effect was stereoselective, since administration of 160 μg of dextrorphan did not alter the nociceptive threshold. Levorphanol at these doses had no systemic effect, since the contralateral saline-injected paws exhibited neither a significant difference between any groups nor a dose-response relationship.

As compared to the contralateral control paws, the inflamed hind paws had significantly ($F[1,21]=91.0; P<0.001$) greater plasma extravasation, as indicated by an accumulation of Evans blue dye in the subcutaneous tissue. However, the carrageenan-induced plasma extravasation was significantly ($F[1,21]=6.47; P<0.01$) inhibited by administration of morphine; there were no differences between the saline-treated paws.

Morphine also produced a significant ($F[1,21]=7.9; P<0.01$) reduction of carrageenan-induced edema. The carrageenan-treated paws of rats given i.v. morphine had significantly ($P<0.01$) as compared to rats given i.v. saline.

This study demonstrates that local administration of EKC and levorphanol into an inflamed paw produces a dose-related analgesia restricted to the injected paw. These effects are opioid receptor-specific, since levorphanol is analgesic while its dextrorotatory isomer, dextrorphan, is inactive. An additional test to determine opioid specificity, naloxone challenge, was contraindicated because of naloxonoe's reported agonist-like effects in this model of inflammation (Rios et al, supra). In addition, morphine suppresses plasma extravasation by 41% and inhibits edema by 32% in CARRA-evoked inflammation.

If opiates acted only in the central nervous system to produce analgesia, then a bilateral analgesic effect should have been observed in both inflamed hind paws, regardless of the site of administration. However, systemic administration of this low dose of EKC had no effect, while peripheral administration into an inflamed paw produced localized analgesia. Additional evidence for lack of a systemic opiate effect is the similar latencies of the SAL-injected contralateral paws of the group receiving local opiate and for the CARRA group receiving no opiate. Finally, the latencies of the SAL-treated paws of the four levorphanol groups were statistically indistinguishable, despite the dose-related analgesia observed in the opiate-treated paws. We interpret these results to indicate that opiate-induced analgesia is due to a peripheral as well as to its well recognized central mechanism of action. The peripheral analgesic effect is observed with both kappa and mu agonists.

The results raise the question of the mechanism of this peripheral opiate effect. Since plasma extravasation is a fundamental step in the development of inflammation, the blockade of edema and hyperalgesia by opiates may be related to an initial opiate blockade of plasma extravasation. The two most likely targets are peripheral terminals of primary afferents and leukocytes, both of which are known to possess opioid receptors (Fields et al, supra; Young et al, supra; Laduron, supra; Wybran, supra). An opioid effect on the nerve terminals may be direct, by modulating nociceptive transmission (Jurna et al, supra; Russell et al, Opiates inhibit the discharge of fine afferent units from inflamed knee Joint of the cat, Neurosci. Lett., 76:107-112 (1987)) or may be indirect, by an anti-inflammatory effect (Letobeck et al, supra and Smith et al, Peripheral opioid receptors located on the rat saphenous nerve, Neuropeptides, 5:217-220 (1984). This last issue is pertinent, since carrageenan-evoked inflammation has a significant neurogenic component (Joris et al, Involvement of the peripheral nervous system in carrageenan-induced inflammation, Abstr. Soc. Neurosci., 13:1017 (1987)). An alternative hypothesis is that the opiate effect on edema and plasma extravasation is due to a CNS alteration of efferent outflow. Since morphine was administered systemically, it remains to be determined whether the suppression of plasma extravasation and edema are related to the peripheral effects of opiates or to their systemic effects.

The existence of a peripheral site of action for opiate-induced analgesia provides a potential target for circulating opioid peptides. Numerous studies have demonstrated that blood-borne levels of opioid peptides increase significantly under conditions of Stress (Mueller, supra) and inflammatory pain (Hargreaves et al, Naloxone, fentanyl and diazepam modify plasma beta-endorphin levels during surgery. Clin. Pharmacol. Ther., 40:165-171 (1986); Joris et al, Behavioral and endocrine correlates of thermal nociception in carrageenan-induced cutaneous hyperalgesia, Abstr. Soc. Neurosci., 12:374 (1986)). However, their physiological role is unclear. The potential role of pituitary β-endorphin (β-END) in modulating pain has been evaluated under conditions designed to stimulate its release and activate endogenous pain suppression systems (Amir et al, Endogenous opioid ligands may mediate stress-induced changes in the affective properties of pain related behavior in rats, Life Sci., 23:1143-1152 (1978a); Amir et al, The pituitary gland mediates acute and chronic pain responsiveness in stressed and non-stressed rats, Life Sci., 24:439-448 (1978b); Marek et al, Dexamethasone reverses adrenalectomy enhancement of footshock-induced analgesia in mice, Pharmacol. Biochem. Behav., 18:167-169 (1983)). These observations may be clinically relevant, since patients pretreated with low doses of dexamethasone have lower levels of circulating β-endorphin and significantly greater levels of post-operative pain as compared to patients treated with placebo (Hargreaves et al, Dexamethasone alters plasma levels of beta-endorphin and post-operative pain, Clin. Pharm. Ther., 42:601–607).

Recent studies have extended these findings by administration of corticotropin-releasing factor (CRF) to post-operative patients. CFR is the endogenous signal for evoking the release of pituitary β-END in response to stressors such as surgery or post-operative pain (Vale et al, Characterization of a 41-residue ovine hypothalamic peptide that stimulates secretion of corticotropin and beta-endorphin, Science, 213:1394–1397 (1981)). Administration of CRF was found to stimulate β-END secretion and significantly reduce post-operative pain in patients following extraction of impacted third molars (Hargreaves et al, Corticotropin releasing factor (CRF) produces analgesia in humans and rats, Brain Res, 422:154–7 (1987)). Results from the present study suggest that one potential target for these circulating opioids is the peripheral modulation of nociception secondary to inflammation.

EXAMPLE 4—IN VIVO STUDIES

The effects of carrageenan-induced inflammation on circulating levels of iB-END and hyperalgesia were evaluated concurrently in awake rats. In all studies, male Sprague-Dawley rats (Charles River, Inc) were housed (lights on 0600–1800) with food and water ad libitum for one week prior to the experiment. In the behavioral study, rats (200–250 g) had jugular catheters implanted under pentobarbital (50 mg/kg; ip) anesthesia two days before the study. The patency of the i.v. catheters were maintained by daily administration of heparin (0.2 ml of 100 U/ml). On the day of the experiment, rats received a subcutaneous (s.c.) injection of either lambda carrageenan (2 mg in 0.1 ml saline; Sigma Chemical Co.) or an equal volume of saline into the plantar surface of the hindpaw (n=8/group). Carrageenan-induced changes in blood-borne iB-END were measured by collection of 1 ml blood samples. Plasma was separated by centrifugation and immediately frozen, while the cells were resuspended in 1 ml of saline and re-injected. Plasma samples were collected before and 2.5 hours after hindpaw injections; at this dose, carrageenan-induced inflammation reaches a plateau from 2 through 4 hours after injection (Hargreaves et al, A new and sensitive method for measuring thermal notiception in cutaneous hyperalgesia, Pain 32:77–88 (1988)). The hyperalgesia due to inflammation was measured in unrestrained rats as described previously (Hargreaves, supra). In brief, rats were placed inside a clear plastic chamber (18 cm×29 cm×12.5 cm) with a glass floor. Following a 5 min habituation period, the plantar surface of the hindpaw was exposed to radiant heat. The paw withdrawal latency, taken as an index of hyperalgesia, was detected automatically by a photocell and presented on an electronic clock.

The presence of a peripheral corticotroph-stimulating factor was evaluated first by determining the effects of hindlimb denervation on the increase in circulating levels of iB-END that was observed during carrageenan-induced inflammation. In the denervation study, rats were anesthetized with pentobarbital and the sciatic and saphenous nerves were ligated with removal of a 5 mm section of the nerves. A separate group of animals underwent a sham surgical procedure; the sciatic and saphenous nerves were exposed but neither ligated nor section. Complete hindpaw anesthesia was verified by the lack of a paw withdrawal reflex following a 20 sec exposure to radiant heat. The cutoff period (20 sec) was imposed to prevent tissue damage; it was more than five standard deviations longer than the mean baseline paw withdrawal latency observed with intact rats in previous studies (mean±SD=9.3±1.3 sec; N=161). One week later, the animals were divided into 4 groups (n=8–10/group) and received s.c. injections into the plantar hindpaw of either lambda carrageenan (2 mg in 0.1 ml saline) or an equal volume of saline. Two of the groups had intact nerves (sham/saline, sham/carrageenan) and the other two were denervated (denervation/saline and denervation/carrageenan). Four hours later, trunk blood was collected into 15 ml polypropylene tubes containing 0.6 ml of 105 EDTA with 15 mg % bacitracin. Plasma was separated by centrifugation and frozen until assayed for iB-END as described below.

COLLECTION OF PERFUSATES

The peripheral release of corticotroph-stimulating factor was evaluated by simultaneously collecting subcutaneous perfusates from both inflamed and contralateral control paws (Joris et al, Local production of immunoreactive bradykinin (iBK) in two models of inflammation, Pain (Abstract Suppl 4): S17 (1987)). The plantar surface of one hindpaw was injected s.c. with 3 mg carrageenan and the contralateral hindpaw was injected s.c. with an equal volume (0.1 ml) of saline; the rats were anesthetized 90 min later. The 3 mg dose of carrageenan was used in anesthetized rats to produce a comparable level of inflammation as that observed following injection of a 2 mg dose into awake animals. Coaxial catheters were inserted subcutaneously at the level of the mid-thigh and extended until they reached the medial-plantar aspect of the heel. The coaxial catheters were constructed of an inner polyethylene tube (PE-50), Clay Adams, N.J.) which extended 5 mm beyond an outer polyethylene tube (PE-240). Sterile saline was pumped through the inner catheter at 0.1 ml/min and perfusate was collected, from 120–210 min after carrageenan injection, by a peristaltic pump connected to the outer catheter. The perfusate samples from the carrageenan-and saline-injected paws were immediately frozen and lyophilized.

PITUITARY CULTURES

The anterior lobe of the pituitary was dissected from male Sprague-Dawley rats (150–200 g) and was enzymatically dispersed according to the method of Vale et al, Culture of enzymatically dispersed anterior pituitary cells: functional validation of a method. Endocrinology 91:562–572 (1972). Approximately 2–4 X$10^4$ cells were plated in 10×35 mm culture dishes (Falcon, Oxnard Calif.) in 2 ml culture medium and grown at 37° C. in 95% air and 5% carbon dioxide. The culture medium consisted of Dulbecco's modified Eagle's medium (Gibco, Grand Island, N.Y.) and (final concentration) contained 105 horse serum, 2% fetal calf serum, 1% MEM non-essential amino acids, 1% hepes 1M, 1% BME vitamin and 1% penicillin/streptomycin (all from Gibco). Release experiments were carried out 7 days after plating. Cultures were washed twice with Hank's balanced salt solution (HBSS) and then exposed to various test substances in 2 ml of HBSS using 3–6 cultures for each treatment. Lyophilized perfusates from carrageenan- and saline-injected paws (equivalent to 1 ml of actual perfusate), ovine corticotropin releasing factor (oCRF), bradykinin, substance P and calcitonin gene-related peptide (CGRP), were dissolved in HBSS immediately prior to application to the cultures (all peptides from Peninsula Labs, San Carlos Calif.). At the end of the two hour release experiment, the media was centrifuged to separate cells. Aliquots of the supernatant were frozen until assayed.

RADIOIMMUNOASSAY

Aliquots of plasma and culture medium were assayed for iB-END using rabbit antiserum (C-55 kindly provided by Dr. Gregory Mueller (Uniformed Services University of the Health Sciences, Bethesda, Md.). The antiserum has been characterized previously for measuring iB-END from plasma samples and pituitary culture medium (Mueller, Attenuated pituitary beta-endorphin release in estrogen treated rats, Proc. Soc. Exp. Biol. Med. 165:75-81 (1980); Mueller, G., Beta-endorphin immunoreactivity in rat plasma: variations in response to different physical stimuli, Life Sci., 29(1981) 1669-1674; Pettibone et al, Alpha adrenergic stimulation by clonidine increases plasma concentrations of immunoreactive beta endorphin in rats, Endocrinology 109:798-802 (1981)).

At a final dilution of 1:125,000, the antiserum binds 30-35% of iodinated N-acetyl-B-END$_{1-27}$ (Peninsula) with a minimum detection limit of 1 fm/tube. The antiserum binds to amino acids #17-25 of beta endorphin and thus equally recognizes the different molecular forms of beta endorphin as well as beta lipotropin (Mueller, Attenuated pituitary beta-endorphin release in estrogen treated rats, Proc. Soc. Exp. Biol. Med. 165:75-81 (1980)). These molecular forms of beta endorphin collectively comprise iB-END. The antiserum does not recognize alpha or gamma endorphin or the enkephalins (Mueller, supra).

EVALUATION OF PEPTIDASE ACTIVITY

Previous studies (DiAugustine et al, Corticotropin/-beta-endorphin immunoreactivity in rat mast cells: peptide or protease, Life Sci. 27:2663-2668 (1980); Jahanke et al, Peptide hormone degradation by a rat mast cell chymase-heparin complex. Life Sci. 29:397-403 (1981); Tsubouchi et al, Degradation of [$^{125}$I ]iodoglucagon by normal rat plasma in radioimmunoassay mixture containing aprotinin and its prevention by p-chloromer-curiphenyl sulfonate and leupeptin, Endocrinology 119:1137-1145 (1986)) have demonstrated that biological samples containing peptidases can produce false-positive measurements of immunoreactive substances, due to degradation of the iodinated tracer. This potential confound is relevant since perfusates from inflamed tissue contain peptidase activity (Costello et al, unpublished observations). Accordingly, we determined whether peptidase activity in carrageenan perfusates contributed to the observed increase in iB-END levels from pituitary cultures. Approximately 8,000 cpm of iodinated N-acetyl-B-END$_{1-27}$ were incubated at 37° C. for 60 min with either 0.05M phosphate buffer or with medium from pituitary cultures. These cultures underwent a standard release experiment with treatments consisting of either 1 nM oCRF or 0.1 ml of reconstituted carrageenan perfusate (equivalent to 1 ml of actual perfusate). Following incubation, the samples were loaded onto an HPLC system (Perkin Elmer, series 400) with a 0.5×25 cm C18 column (Axiom) and eluted with a linear gradient (1%/min with a flow of 1 ml/min) of acetonitrile in 0.05% trifluoroacetic acid. Since the elution profile of peptides in a reverse phase HPLC column is determined by their amino acid composition (Meek et al, Factors affecting retention and resolution of peptides in high performance liquid chromatography, J. Chromatog. 211:15-28 (1981)), a change in the elution profile of iodinated B-END is a measure of peptidase activity. The elution profile was determined by measuring the radioactivity of each fraction (1 ml) in a gamma counter (Beckman Inc).

STATISTICS

Statistical analysis was carried out by analysis of variance for overall effect, with Duncan's multiple range test for comparisons between groups (Winer, Statistical Principles in Experimental Design, McGraw-Hill, New York. (1971). An analysis of covariance was used to remove baseline differences in the levels of iB-END in the first experiment. A difference was interpreted to be significant if the probability that it had occurred due to chance alone was less than 5% ($P<0.05$). Data are presented as the mean±s.e.m.

As compared to the paw withdrawal latencies of the saline-injected group, the carrageenan-treated group had significantly (P[600.01) shorter latencies at 2.5 hours after injection. Concurrent with the onset of hyperalgesia, levels of iB-END were significantly greater ($P<0.05$) in the carrageenan group as compared to the saline group.

The increase in iB-END during carrageenan-induced inflammation could be either due to pain sensation produced by neural activity at the site of inflammation or to peripheral release of a corticotroph-stimulating factor from inflamed tissue. These hypotheses were evaluated by denervating the hindlimb one week prior to injection of either carrageenan or saline. Levels of iB-END in sham surgery rats 4 hours after injection of carrageenan were significantly greater ($P<0.05$) than sham surgery rats injected with saline. There were no differences between sham and denervated rats who were injected with saline. In addition, denervation did not block the increase in carrageenan-induced iB-END levels with denervation/carrageenan rats having significantly ($P<0.01$) greater levels than denervation/saline rats.

The presence of a peripheral corticotroph-stimulating factor was evaluated by collecting s.c. perfusates from carrageenan- and saline-injected paws and determining their ability to release iB-END when applied to pituitary cultures. Treatment with perfusates from carrageenan-treated paws resulted in significantly greater iB-END levels as compared to either basal release (depicted as the horizontal line; (P₤600.01) or to perfusates from saline-treated paws (P₤600.01). In this experiment, perfusates from saline-treated paws produced a significant (P₤600.05) release of iB-END as compared to basal release. Application of oCRF to the cultures caused significant increases at 0.1 nM (P₤600.05) and 10 nM (P₤600.01).

We next determined whether the increase in levels of iB-END measured in pituitary culture media was due to peptidase activity. The absences of differences in the three group's HPLC profiles of iodinated beta endorphin indicates that peptidase activity does not account for the observed increase in iB-END.

For treatments incubated in the presence of calcium, perfusates from carrageenan-injected paws had significantly greater levels of iB-END as compared to basal release (P₤600.01) and to saline perfusates (P₤600.01).

The releasing activity in the carrageenan perfusate was completely blocked in the absence of calcium. In addition, carrageenan had no releasing effect of its own when administered directly to cultures containing calcium.

In separate experiments, there was no effect of either bradykinin, substance P or CGRP on release of iB-END from pituitary cultures (Table 5) below.

TABLE 5

EFFECTS OF BRADYKININ, SUBSTANCE P, CALCITONIN GENE-RELATED PEPTIDE AND oCRG ON RELEASE OF IMMUNOREACTIVE BETA ENDORPHIN FROM RAT ANTERIOR LOBE PITUITARY CULTURES[1]

| Peptide | $10^{-10}$M | $10^{-9}$M | $10^{-8}$M | $10^{-7}$M | $10^{-6}$M |
|---|---|---|---|---|---|
| Bradykinin | — | 5.4 ± 5.6% | −18.0 ± 15.0% | −36.0 ± 6.0% | — |
| Substance P | — | — | −33.4 ± 12.5% | — | −64.1 ± 13.0% |
| CGRP | — | — | −54.7 ± 8.0% | — | −9.0 ± 6.8% |
| CRF | 389.0** ± 14.0% | 614.6** ± 6.2% | 789.0** ± 15.3% | — | — |

[1]data expressed as % increase over basal levels: mean ± s.e.m.
**significantly greater than sal levels (0.5 ± 0.04 pm/well): $p < 0.01$ The results of this study indicate that a peripheral corticotroph-stimulating factor is released from inflamed tissue. This conclusion is based on two converging lines of evidence gathered from in vivo studies using rats with denervated hindlimbs and in vitro studies using subcutaneous perfusates applied to pituitary cell cultures.

The first line of evidence arises from the in vivo studies. The increase in blood-borne levels of iB-END during carrageenan-induced inflammation may be due to either a stressor such as the pain and hyperalgesia that accompany the inflammation, or to an endocrine substance released from inflamed tissue. Since removal of hindlimb afferent input failed to block the increase in circulating iB-END, an endocrine substance is implicated. The reason for higher levels of iB-END in the denervation/carrageenan as compared to the sham/carrageenan group is unclear; subsequent experiments replicated the finding of an iB-END increase in denervated rats, with levels never exceeding those observed in sham rats treated with carrageenan. The increase in iB-END was observed only in the denervation/carrageenan group and was not seen in the denervation/saline group. This indicates that denervation itself does not constitute a stressor capable of stimulating the pituitary-adrenal axis. Although the experiment does not exclude a possible CNS activation of the pituitary-adrenal axis (e.g., due to visual cues of peripheral inflammation), the increase in levels of iB-END was most likely due to a humoral component of carrageenan-induced inflammation.

The second line of evidence supporting the hypothesis of a peripheral corticotroph-stimulating factor comes from the in vitro studies. Perfusates collected from carrageenan-inflamed tissue significantly stimulate the release of iB-END from pituitary cultures. The amount of the factor collected in a 10 minute period has releasing activity intermediate between 0.1 nM and 10 nM of synthetic oCRF. Perfusates from carrageenan-treated hindpaws have significantly greater amounts of peripheral corticotroph-stimulating factor as compared to perfusates collected from contralateral, saline-treated hindpaws. The low, but detectable amount of peripheral corticotroph-stimulating factor observed in the perfusates from saline-treated hindpaws may be due to tissue damage secondary to surgical implantation of the catheters.

The increase in iB-END is due to neither peptidase degradation of iodinated B-END tracer nor to a direct action of carrageenan on the pituitary cultures. The releasing activity of the peripheral corticotroph-stimulating factor is completely blocked in the absence of calcium. This calcium dependency is also observed with other corticotroph stimulating agents such as oCRF (Vale et al, Characterization of a 41-residue ovine hypothalamic peptide that stimulates secretion of corticotropin and beta-endorphin, Science, 213:1394-1397 (1981)). An additional interpretation from the calcium experiment is that the measured levels of iB-END could not be of peripheral leukocyte origin. Leukocytes have been reported to contain iB-END (Blalock et al, Human leukocyte interferon:structural and biological relatedness to adrenocorticotropic hormone and endorphins, Proc. Natl. Acad. Sci. USA 77:5972-5974 (1980)), and it was a possibility that the iB-END was simply collected in the perfusates and measured in the pituitary culture media. This possibility can be rejected since it predicts that the observed iB-END levels should not have differed between the calcium and calcium-free pituitary culture groups; both groups receiving aliquots from the same pool of perfusate. Taken together, the results from the in vivo and in vitro studies suggest that an extrahypothalamic substance, originating from the inflamed tissue, stimulates the pituitary-adrenal axis during carrageenan-induced inflammation.

The potential physiologic functions of a peripheral corticotroph-stimulating factor released from inflamed tissue require further study. It is possible that the pituitary-adrenal response to a stressor is a result of both hypothalamic (i.e., release of CRF) and extra-hypothalamic input, with stressors differing in their activation of these two systems. Brief non-injurious stressors such as immobilization may activate primarily the hypothalamic control systems. Conversely, inflammation due to tissue damage may stimulate release of hypothalamic and peripheral factors to coordinate the pituitary-adrenal response to stress.

The actual physical structure of the peripheral corticotroph-stimulating factor remains to be determined. Although immunoreactive bradykinin is significantly elevated in carrageenan persuates (Joris et al, supra) and bradykinin can stimulate in vitro release of iB-END (Matsumura et al, In vivo and in vitro effects of bradykinin on the release of beta-endorphin-like immunoreactivity, Neuroendocrinology 41:101-106 (1985); Okajima et al, Bradykinin-induced ACTH release from rat pituitary tissue in vitro, Neuroendocrinology 43:336-339 (1986)), the present studies failed to detect a releasing effect using bradykinin standard. It is possible, however, that this lack of an effect may be due to peptide absorption; thus bradykinin cannot be excluded as a potential tissue factor. It is possible that the peripheral corticotroph-stimulating factor is of immune origin. Carrageenan-induced inflammation has a substantial immune component (Flower et al, A comparison of the acute inflammatory response in adrenalectomized and sham-operated rats, Br. J. Pharmac. 87:57-62 (1986)). In addition, several (Berkenbosch et al, Corticotropin releasing factor producing neuron in the rat activated by interleukin I, Science 238: 524-526 (1988); Bernton et al, Release of multiple hormones by direct action of interferon I on pituitary cells, Science 238:519-521 (1987); Farah et al, Thymosin fraction V stimulates secretion of immunoreactive beta endorphin in mouse corticotropic tumor cells, J. Neurosci. Res. 18:140-146 (1987)), but not all (Sapolsky et al, Interleukin I stimulates the secretion of hypothalamic corticotropin-releasing factor, Science 238:522-524 (1987)), studies have demonstrated that substances of leukocyte origin can stimulate pituitary corticotroph secretion. Alternatively, the peripheral corticotroph-stimulating factor could arise during plasma extravasation or from other inflammatory processes, possibly including substances derived from endothelial breakdown.

It is possible that the factor described in the present study is related to a peripheral corticotroph-stimulating factor previously reported to be released following tissue injury (Carr et al, Burn-induced analgesia and endorphin secretion: Analysis in a pituitary autotransplant model, Pain (Abstract Suppl. 4):S413 (1987); Gordon, M. An evaluation of afferent nervous impulses in the adrenal cortical response to trauma, Endocrinology 47:347-350 (1950); Lymangrover et al, Tissue CRF: an extra-hypothalamic corticotropin releasing factor (CRF) in the peripheral blood of stressed rats, Neuroendocrinology 12:225-235 (1973); Lymangrover et al, The Physiological regulation of tissue-CRF, Neuroendocrinology 13:234-245 (1973/4); Simpson et al, ACTH regulation of tissue-CRF, Neuroendocrinology 31:210-214 (1980).

Lymangrover et al detected such a factor in the blood of rats who had undergone laparotomies with intestinal exteriorization and manipulation. Five hours after the laparotomies, the blood was injected into recipient rats, resulting in an increase in circulating corticosterone. The increase in corticosterone required an intact pituitary in the recipient rat, implying that the factor acts at the level o f the pituitary corticotroph cell (Lymangrover et al, Tissue CRF: an extra-hypothalamic corticotropin releasing factor (CRF) in the peripheral blood of stressed rats, Neuroendocrinology 12:225-235 (1973); Lymangrover et al, Physiological regulation of tissue-CRF, Neuroendocrinology 13:234-245 (1973/4); Simpson et al, ACTH regulation of tissue-CRF, Neuroendocrinology 31:210-214 (1980)). In addition to surgical trauma, thermal injury can also evoke peripheral release of a CRF-like factor.

In response to exposing a denervated hindpaw to intense thermal stimulation, the pituitary-adrenal axis is stimulated to the same extent as that observed in rats with intact hindpaws (Gordon, supra). In addition, rats with autotransplantation of the pituitary to the kidney capsule can no longer respond to hypothalamic stimuli, but still demonstrate a 4–5 fold increase in circulating iB-END in response to thermal injury (Carr et al, supra). These findings indicate that both surgical trauma and thermal injury are similar to carrageenan-induced inflammation for the ability to evoke the peripheral release of a corticotroph-stimulating factor.

Assuming that these peripheral factors are related, the present study extends the previous work by 1) developing an acute model of moderate inflammation which allows collection of high levels of the peripheral corticotroph-stimulating factor by directly perfusing inflamed tissue, 2) using within-animal controls by collecting perfusates from both inflamed and contralateral saline-injected hindpaws, and 3) employing a pituitary culture as a bioassay for demonstrating the calcium dependency of the releasing activity. These issues are important for future studies directed at identifying the physicochemical properties of this peripheral corticotroph-stimulating factor.

EXAMPLE 5

Measurement of immunoreactive bradykinin. The blood samples were collected and processed for measuring immunoreactive bradykinin according to a technique modified from Mashford and Roberts (Mashford, M. et al, Determination of blood kinin levels by radioimmunoassay, Biochemical Pharmacol 21:2727-35 (1972)).

The intravenous line was cleared by collection of blood into an evacuated tube, which was discarded. Immediately after the first collection, blood was collected into an evacuated 15 ml polypropylene tube containing 10 ml of 100 mmol/L orthophenanthrolene (a kininase inhibitor, Mashford et al, supra) in ethanol. The tube was agitated continuously during collection to ensure mixing of blood with the solution of orthophenanthrolene/ethanol. With this technique, 3 to 4 ml of blood can be collected during a brief (<3 to 5 seconds) period. The volume of the blood sample was calculated by taking the difference between the presample and postsample weights of the collection tube. The samples were then centrifuged at 2000 rpm for 20 minutes and supernatants were dried in a vacuum centrifuge. The dried samples were stored at $-70°$ C. until assayed.

The samples were resuspended in 0.3 ml of ethanol. Solubilization was enhanced by a 2 to 3 hour incubation period followed by sonication. Samples were than centrifuged (2000 rpm for 20 minutes) and aliquots of the supernatant were pipetted into the RIA. The assay conditions consisted of bradykinin standard (Peninsula Laboratories, Inc., Belmont, Calif.) or unknown sample, together with 1:230,000 final dilution of antiserum JP-1 (a previously characterized bradykinin antiserum, Proud, D. et al, Kinins are generated in vivo following nasal airway challenge of allergic individuals with allergen. J Clin. Invest, 72:1678-85 1983) and 10,000 cpm of iodinated [TYR$^1$]-bradykinin in an assay volume of 0.5 ml. The RIA buffer consisted of 0.1% lysozyme, 0.2 mol/L Tris buffer, 0.1 mol/L EDTA, and 0.01% sodium azide with pH set at 6.4. The standard curve of the bradykinin RIA was assayed in buffer containing an equivalent amount of ethanol as in the unknowns (20% final concentration). The minimum detection limit was 1 femtomole/tube and the intrassay and interassay variation was less than 6% and 12%, respectfully. The antibody does not cross-react with mepivacaine, midazolam, methylprednisolone, or aspirin, medications that were taken by the patients.

The bradykinin antiserum binds near the C-terminal position of bradykinin and thus detects bradykinin related peptides and its precursor, kininogen (Proud, D. et al, supra). Because kininogen is present in blood at a concentration several orders of magnitude greater than is bradykinin,[29] it is necessary to use a collection technique that removes the kininogen. To determine that ethanol preciciptates kininogen, gel chromatography was performed to separate kininogen-sized immunoreactive material. Blood (totaling 50 ml) was collected according to the ethanol technique described above and an additional 2 ml of blood was collected in evacuated glass tubes containing 0.07 ml of 15% EDTA. The resuspended ethanol samples or plasma were loaded onto a Sephadex G-50 (Pharmacia Fine Chemicals, Piscataway, N.J.) column (0.9 cm by 60 cm) and eluted with buffer (0.1N acetic acid), with collection of 1 ml fractions. The column had been characterized previously for its void volume (dextran blue), salt volume (cobalt chloride, and elution position according to authentic bradykinin standards.

ACUTE CLINICAL INFLAMMATION

The effect of surgical trauma and acute inflammation on circulating levels of immunoreactive bradykinin was evaluated in patients undergoing oral surgery. On the day of surgery an intravenous line was established in a vein in the antecubital fossa, and after a 20-minute recovery period blood samples were drawn as described above. Duplicate blood samples were collected before surgery, after local anesthesia, during surgery (at 20 and 30 minutes), at the end of surgery, and after surgery (30, 60, 90, 120, 150, and 180 minutes). Approximately 80% of the duplicate samples had levels of immunoreactive bradykinin within 10% of each other; in the remaining cases the lower of the duplicate samples was taken to represent the patient's sample. The surgical removal of four impacted third molar was performed under local anesthesia (3% mepivacaine) with intravenous midazolam sedation as indicated. Patients did not take postoperative medications until after completion of the study. The mean duration of surgery was 39.4±13 minutes. Patients were given postoperative analgesics at the completion of the study after all blood collections. The 19 patients (seven males and twelve females) participating in the oral surgery study had a mean age of 21±4.5 years and their medical history was unremarkable.

CHRONIC CLINICAL INFLAMMATION

The effect of chronic inflammation on circulating levels of immunoreactive bradykinin was evaluated in patients with rheumatoid arthritis by comparison with normal healthy volunteers. The diagnosis of rheumatoid arthritis had been confirmed previously by a rheumatologist according to standard clinical, radiographic, and laboratory criteria. The 21 patients with rheumatoid arthritis (six males and 15 females) ranged in age from 24 to 78 years (mean 47 years). The mean duration of the disease was approximately 17 years. More than 90% of the patients reported to be in pain on the day of the blood sample collection. Medications (and percent of the study sample) reported by the patients included prednisone (50%), methotrexate (44%), aspirin-like drugs (100%), hydroxychloroquine sulfate (Plaquenil) (22%), and gold (22%). The control volunteers (eight men and 13 women) were selected on the basis of an unremarkable medical history; their mean age was 38 years (range 27 to 59 years). An intravenous needle was established in a vein in the arm and one blood sample was drawn as described above.

RAT CARRAGEENAN MODEL OF INFLAMMATION

The next study determined whether elevated levels of circulating immunoreactive bradykinin were detectable in a rat model of inflammation. Male Sprague-Dawley rats (200 to 250 gin; Charles River Breeding Laboratories, Inc., Wilmington, Mass.) were implanted with intravenous catheters in the jugular vein under pentobarbital anesthesia (50 mg/kg). Two days later the animals were divided into two groups (n=8/group) that received a subcutaneous injection (0.1 ml) into the plantar surface of the hindpaw of either 2 mg carrageenan (Sigma Chemical Co., St. Louis, Mo.) or saline solution Carrageenan-induced inflammation is a standard animal model of inflammation and is highly predictive of anti inflammatory drug activity of human conditions of inflammation (Otterness, I. et al, Laboratory models for testing nonsteroidal antiinflammatory drugs, In: Lombardino, J., cd. Non-steroidal antiinflammatory drugs. New York: Wiley, 112-252 (1985)). Blood samples (0.5 ml) were collected through the jugular catheters in awake rate into 2 ml of 100 mmol/L orthophenanthrolene in ethanol at a baseline time and 2½ hours after injection of carrageenan. The samples were processed and assayed for immunoreactive bradykinin as described above. Behavioral hyperalgesia was assessed as described previously (Hargreaves et al, supra). In brief, unrestrained animals were placed inside a clear plastic chamber (18 cm by 12.5 cm) with a glass floor. After a 5-minute habituation period, animals typically stopped exploratory movements and were engaged in bouts of self-grooming. At this time the plantar surface of the hindpaw was exposed to a beam of radiant heat applied through the glass floor. The paw withdrawal latency was automatically detected by a photocell. Previous studies have demonstrated this method to be sensitive to detecting the effects of analgesic and antiinflammatory drug (Hargreaves, K. et al; A new and sensitive method for measuring thermal nociception in cutaneous hyperalgesia, Pain; 32:77-88).

IN VITRO BRADYKININ SYNTHESIS

Because the constituents of the bradykinin system are in blood, an in vitro assay based on fresh human plasma was used to screen for compounds that inhibit the synthesis of bradykinin. Blood was collected in 0.07 ml of 15% EDTA, and the plasma was separated by centrifugation. To interpret changes in immunoreactive bradykinin as the result of changes in synthesis, captopril (1 mmol/L) and EDTA (1 gm/dl) were added to minimize kininase degradation of bradykinin (Garcia Lemc, J., Bradykinin system. In: Bonn G., cd. Handbook of experimental pharmacology, vol. 50 New York: Springer-Verlag, 464-521 (1978); Caretero, O. et al, Roll of kinins in the pharmacological effects of converting enzyme inhibitors, In: horovitz Z, cd. Angiotensin converting enzyme inhibitors. Baltimore: Urban and Schwarzenberg 105-121 (1981); Ikenaka, T. et al, Chemical structure and inhibitory activities of soybean proteinase inhibitors, In: Fritz H., Tschesche H., Green L., Truschcit E., eds. Proteinase Inhibitors. New York: Springer-Verlag, 325-43 (1974)). Kallikrein was maximally activated by the addition of 2 mg carrageenan (Sigma Chemical Co., St. Louis, Mo.) in a total reaction volume of 0.5 ml. SBT1 (1 mg; Sigma Chemical Co.) was selected for evaluation of inhibition of kallikrein activity based on its spectrum of antiserine protease activity (Ikenaka, T. et al, supra). The assay was incubated for 30 minutes and was terminated by the addition of 2 ml of ethanol. The samples were then processed as described above.

EVALUATION OF SBTI ANALGESIA

The antiinflammatory effects of SBTI were then evaluated in the rat model of carrageenan-induced inflammation by observers blinded as to treatment allocation. Rats were divided into two groups (n=7 to 8/group) by the subcutaneous injection into the plantar hindpaw of either 0.2 mg SBTI or 1 mg SBTI. The contralateral hindpaw received a subcutaneous plantar injection of saline solution in an equivalent volume (0.1 ml). Ten minutes later all animals received a subcutaneous plantar injection into both hindpaws of 2 mg carrageenan. Animals were evaluated for behavioral hyperalgesia 2 hours after injection of carrageenan.

STATISTICAL EVALUATION

Statistical significance was determined by ANOVA for repeated measures to determine overall effect followed by Duncan's multiple range test to determine the source of the differences for changes in circulating levels of immunoreactive bradykinin and paw withdrawal latencies in the rat carrageenan study. A one-way ANOVA was used to evaluate differences in the in vitro synthesis of immunoreactive bradykinin. An independent t test was used to evaluate differences in the rheumatoid arthritis study. Pearson's product moment tests were conducted to measure the association between circulating immunoreactive bradykinin and patient sex and age. Differences were accepted as significant if the probability that they occurred as a result of change alone was less than 5% ($p<0.05$). Data are presented as the mean±SE.

COLLECTION AND MEASUREMENT OF IMMUNOREACTIVE BRADYKININ

The chromatographic profiles of immunoreactive bradykinin after blood was collected in EDTA or ethanol were analyzed. Blood collected in EDTA shows two major peaks of immunoreactivity. The first peak is of large molecular weight, because it is near the void volume of the G50 column (molecular weight cutoff of G50 is 30,000). This material consists primarily of kininogen (molecular weight approximately 80,000), because incubation with trypsin causes a very large increase in bradykinin-sized material when the digested first peak is reassayed after subsequent gel chromatography (data not shown). The second peak of immunoreactive material in the EDTA plasma sample coelutes with authentic bradykinin. Blood collected with the ethanol procedure (dark profile) results in a peak of immunoreactivity that coelutes with authentic bradykinin standard. However, there is no kininogen-size immunoreactivity.

BRADYKININ LEVELS DURING AND AFTER ORAL SURGERY

Oral surgery resulted in a significant elevation in intraoperative circulating levels of immunoreactive bradykinin compared with baseline levels (15.3±3.4 fmol/ml). Intraoperative levels of immunoreactive bradykinin were significantly greater at both the 20-minute (67.1±9.3 fmol/ml; $p<0.01$) and 30-minute (39.7±12.1 fmol/ml; $p<0.05$) time points. Levels tended to remain elevated above baseline throughout the postoperative sampling period, although differences were not significant.

BRADYKININ LEVELS DURING CHRONIC INFLAMMATION

Figure 3:
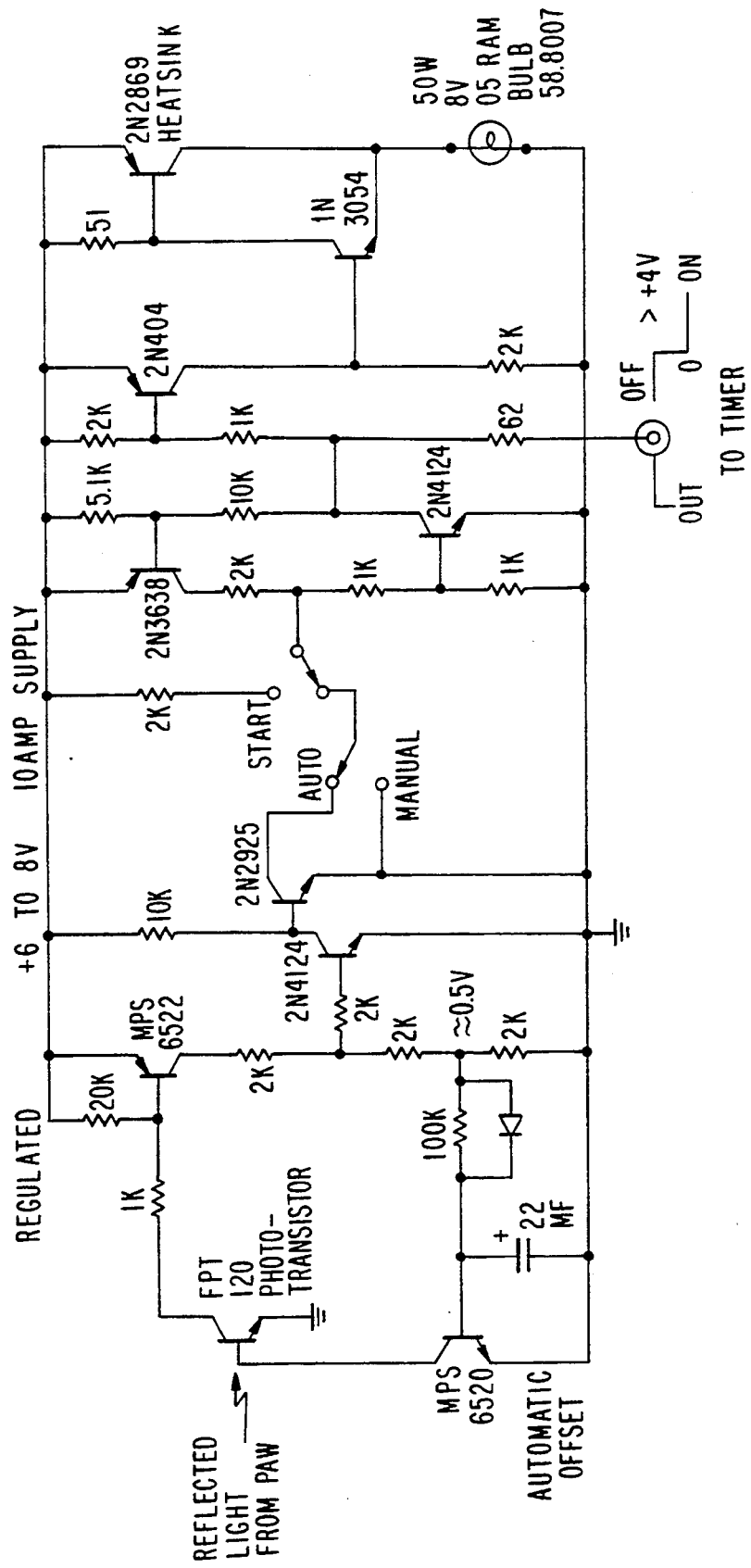
FIG. 3 depicts a specific embodiment of the movable enclosure containing the means for generating the light beam, the means for starting the operation, the means for stopping the time measuring means and the light generating means and deactivating the light detecting means.

Circulating levels of immunoreactive bradykinin in patients with chronic inflammation as a result of rheumatoid arthritis were compared with those of control volunteers. Patients with rheumatoid arthritis had significantly ($p<0.01$) greater blood levels of immunoreactive bradykinin (27.6±5.9 fmol/ml) compared with control patients (9.6±1.4 fmol/ml) (FIG. 3). Scatter plots of the patients with rheumatoid arthritis and the normal volunteers showed no association between levels of immunoreactive bradykinin and age ($r=0.005$; difference not significant) or levels of immunoreactive bradykinin and sex ($r=0.021$; difference not significant).

BRADYKININ LEVELS IN AN ANIMAL MODEL OF INFLAMMATION

Increases in blood levels of immunoreactive bradykinin were also demonstrated in the rat model of carrageenan-induced inflammation. At the baseline time point the paw withdrawal latencies and blood levels of immunoreactive bradykinin were similar between a carrageenan and saline groups. However, 2½ hours after injection, carrageenan-treated rats had significantly shorter paw withdrawal latencies ($p<0.01$) and significantly greater circulating levels of immunoreactive bradykinin ($p<0.01$) compared with saline-treated rats.

SUPPRESSION OF IN VITRO BRADYKININ FORMATION BY SBTI

Antagonism of bradykinin formation by SBTI was demonstrated in vitro with fresh human plasma (Table 1). The addition of carrageenan significantly increased the levels of immunoreactive bradykinin compared with saline-treated samples at both 4° C. ($p<0.01$) and 20° C. ($p<0.01$) incubation temperatures. This increase in immunoreactive bradykinin was completely blocked by the addition of SBTI to the carrageenan-plasma solution at both the 4° C. ($p<0.01$) and 20° C. ($p<0.01$) temperatures (Table 6).

TABLE 6

| | In vitro effects of SBTI (0.5 mg) on carrageenan (2 mg)-evoked increase in immunoreactive bradykinin from human plasma (0.5 ml) | | | |
|---|---|---|---|---|
| | 4° C. (pm/ml) | | 20° C. (pm/ml) | |
| Plasma plus | 0 Min | 30 Min | 0 Min | 30 Min |
| Saline | 9.08 ± 0.40 | 10.40 ± 0.20 | 10.50 ± 0.38 | 13.62 ± 0.40 |
| Carrageenan | — | 15.00 ± 0.40* | — | 18.16 ± 0.68* |
| Carrageenan with SBTI | — | 9.30 ± 0.68 | — | 9.30 ± 0.68 |

*$p < 0.01$ vs saline at 30 minutes.
$p < 0.01$ vs carrageenan at 30 minutes.

The results of this study indicate that blood-borne levels of immunoreactive bradykinin are significantly elevated in three models of inflammation. Furthermore, an agent that blocks synthesis if immunoreactive bradykinin in vitro possesses analgesic activity when evaluated in vivo.

The ethanol-blood collection procedure was validated after gel chromatography. Despite the fact that kininogen is present several orders of magnitude greater than bradykinin, (Garcia, supra) only the smaller molecular weight of bradykinin-sized material is detectable after ethanol precipitation. This immunoreactive material, recovered in the ethanol supernatant, coclutes with bradykinin standard and many contain extended forms of bradykinin. In contrast, the collection of blood in EDTA illustrates technical difficulties that can arise when attempting to measure accurately circulating levels of immunoreactive bradykinin. First, an early large peak of immunoreactivity is present that consists primarily of kininogen. A second peak of immunoreactivity is present that resembles authentic bradykinin in size. The magnitude of the second EDTA peak, compared with the peak observed with ethanol collection, is due to the continued in vitro synthesis of immunoreactive bradykinin that occurs during collection and processing of blood with EDTA. To measure circulating immunoreactive bradykinin accurately, it is necessary to use a collection procedure that inactivates and precipitates the key components of the bradykinin cascade, namely kininogen, kallikrein, and the kininases.

The present study indicates that the bradykinin system is active in acute and chronic models of inflammation. In the acute inflammation study, surgery results in a threefold to fourfold increase in blood-borne immunoreactive bradykinin compared with the baseline values. In the chronic inflammation study, patients with rheumatoid arthritis have circulating levels of immunoreactive bradykinin approximately twofold to threefold treater than levels observed in control patients. These findings suggest that bradykinin is synthesized and released during clinical inflammation in quantities sufficient to be detected in the vascular compartment. Because of the known proinflammatory pharmacology of bradykinin (Dawson, W. et al, Inflammation—mechanisms and mediators, In: Lombardino J, cd. Nonsteroidal antiinflammatory drugs. New York. Wiley, 76–101 (1985); Basran, G., et al, Evidence in man of synergistic interaction between putative mediators of acute inflammation and asthma. Lancet, 1:935–7 (1982); Mense, S., Sensitization of group IV muscle receptors to bradykinin by 5-hydroxytryptamine and prostaglandin E, Brain Res; 225:95–105 (1981); Lim, R. et al, Pain and analgesia evaluated by the intraperitonical bradykinin-evoked pain method in man, Clin Pharmacol Ther; 8:521–42 (1967); Coffman, J., The effect of aspirin in pain and hand blood flow responses to intra-arterial injection of bradykinin, Clin. Pharmacol Ther,. 7:26–37 (1966); Garcia et al, supra), these results suggest that the bradykinin system is actively involved in the pathophysiologic processes of inflammation. In the rat study, carrageenan resulted in an approximate twofold increase in immunoreactive bradykinin levels, which occurs in parallel with the development of behavioral hyperalgesia.

Given the short half-life of the bradykinin in blood, (Ferreira, S. et al, The disappearance of bradykinin and eledoisin in the circulation and vascular beds of the cat. Br. J. Pharmacol 30:427–25 (1967)) it is reasonable to assume that basal levels of immunoreactive bradykinin are very low. In the present studies, basal levels often were near the minimum detection limit of the RIA. However, during inflammation both the process of plasma extravasation and the resulting activation of the bradykinin cascade contribute to a high local concentration of immunoreactive bradykinin in inflamed tissue. We have previously observed that immunoreactive bradykinin levels in subcutaneous perfusates of carrageenan-injected tissue range from approximately 500 to 1000 fmol/ml during the course of inflammation (Joris, J. et al, Local production of immunoreactive bradykinin in two models of inflammation (abstr), Pain; 4 (suppl): S17 (1987)). Although these perfusate levels are 15 to 30 times greater than the basal blood-borne levels observed in the present study, they still substantially underestimate the actual tissue levels caused by the diluting effect of the saline perfusate. Thus the fifteen-fold to thirtyfold value represents a minimal estimate of the actual concentration gradient of immunoreactive bradykinin between inflamed tissue and the vascular compartment. In addition to this local generation of immunoreactive bradykinin from inflamed tissue, some activated kallikrein may also circulate, leading to continued release of immunoreactive bradykinin. These findings indicate that, despite its short half-life, blood-borne levels of immunoreactive bradykinin appear capable of increasing severalfold during the process of inflammation.

A major implication from the present study is the potential for developing a new class of analgesic-antiinflammatory drugs. SBTI blocks immunoreactive bradykinin synthesis from human plasma in vitro and possesses analgesic activity in vivo. These finding extend previous reports on SBTI blockade of edema in carrageenan-induced inflammation (Van Arman, C. et al, Some details of the inflammation caused by yeast and carrageenan. J Pharmacol Exp. Ther.; 150:328–34 (1965)). (Ferreira, A. et al, Prostaglandins and signs and symptoms of inflammation. In: Robinson H., Vanc J. eds. Prostaglandin synthetase inhibitors, New York: Raven Press. 175–87 (1974)). Based on the results of the present clinical studies, kallikrein inhibitors may be useful as analgesic-antiinflammatory drugs for treatment of acute and chronic inflammation.

The in vitro blockage of bradykinin synthesis may prove to be of predictive value for initial screening of inhibitors. It is important that this class of potentially useful drugs be evaluated in an animal model of hyperalgesia secondary to inflammation, such as the rat carrageenan model used in the present study. Similar to the nonsteroidal antiinflammatory drugs, (Taber, R., Pridictive value of analgesic assays in mice and rate. In: Braude M., Harris L., Smith J., Villarreal J., eds. Narcotic antogonists, vol. 8. Advances in biochemical psychopharmacology. New York: Raven Press (1974):191–211). it is unlikely that these drugs would be active on traditional animal analgesic screening assays (i.e., the hot plate and tail flick tests).

The experimental design used in the rat SBTI study allows within-animal comparisons by injecting the test drug into one of two inflamed hindpaws. In the present study, one hindpaw was pretreated with saline solution; 10 minutes later both hindpaws were injected with carrageenan. If SBTI-induced analgesia was the result of a systemic action, the paw withdrawal latencies of the SBTI and saline-treated paws should not differ. Because SBTI-injected paws had withdrawal latencies significantly longer than the contralateral saline-injected paws, we can conclude that SBTI has a peripheral site of action in addition to the established peripheral site.

Although SBTI has significant analgesic activity in rats, it would not be practical as an analgesic drug. Instead the role of SBTI in subsequent drub development may be viewed as analogous to that of the snake venom peptides isolated from Bothropsjararaca (Ferreira, S., A bradykinin-potentiating factor (BPF) present in the venom of Bothropsjaaruruca. Br. J Pharmacol (1965):24:163–9). The venom peptides were found to inhibit the protease angiotensin-converting enzyme. Identification of the pharmacology and biochemistry of these peptides led to the development of captopril, the antihypertensive drug that is a selective and potent inhibitor of angiotensin-converting enzyme (Cushman, D. et al, Angiotensin converting enzyme inhibitors: evolution of new class of antihypertensive drugs. In: Horowitz A., cd Angiotension converting enzyme inhibitors. Baltimore: Urban and Schwarzenberg, (1981): 105-21).

In a similar fashion, SBTI may serve as a prototype for developing selective inhibitors of the protease kallikrein. The development of selective kallikrein inhibitors may lead to a new class of analgesic-antiinflammatory drugs.

The invention now being fully described, it will be apparent to one of ordinary skill in the art that many changes and modifications can be made thereto without departing from the spirit or scope of the invention as set forth therein.

We claim:

1. In a high sensitivity apparatus for determining the in vivo response to thermal stimulation in an unrestrained subject within a predetermined space which permits the selective application of radiant heat to a predetermined situs of the subject by means of a light beam, the combination comprising
    means for measuring time;
    movable means for generating a light beam;
    means for detecting said light beam, said detecting means being positioned so that it can detect the withdrawal of the situs from the path of said light beam and said detecting means also being isolated from said light beam generating means;
    means for stopping said time measuring means, and said light beam generating means and for inactivating said detecting means, all said means being electrically interconnected, said stopping means being automatically activated by said detecting means upon situs withdrawal;
    means for simultaneously starting said time measuring means and said light beam generating means and for activating said detecting means, all said means being electrically interconnected, whereby when said light generating means is aimed at the predetermined situs and positioned at a distance effective to locally provide radiant heat to said situs and said starting means is activated, the light beam elicits from said subject after a latency time period a spontaneous situs withdrawal response thereof which is detected by said detecting means, said time measuring means, said generating means, said detecting means, said stopping means and said starting means being part of an electrical circuit which is to be connected to a power source prior to use.

2. The apparatus of claim 1, further comprising
    a movable container wherein said light beam generating means, said detecting means and said stopping means are located, said movable container being provided with a light beam window, and said light beam generating means positioned so that the beam travels in the direction of said window and through said window; and
    said starting means being accessible from a position exteriorly located with respect to said movable container.

3. The apparatus of claim 1, further comprising means for receiving and storing an output signal of said time measuring means.

4. The apparatus of claim 3, further comprising computing means for comparing successively obtained time measuring means output signals.

5. The apparatus of claim 1, further comprising
    means for receiving and displaying an output signal of said time measuring means.

6. The apparatus of claim 2, wherein said electrical circuit is to be connected to a power supply of direct current providing about 0.5 to 10 volts at about 25 to 200 amps;
    said light beam generating means is a focused light bulb of about 6 to 8 volts and about 25 to 75 watts;
    said light detecting means is a phototransistor; and
    said window is about 2 mm to 20 mm wide.

7. The apparatus of claim 1 for determining hyperalgesia in an experimental animal, further comprising
    a light beam transparent base having a top surface upon which to deposit the experimental animal, and a bottom surface in the vicinity of which is positioned said light beam generating means; and
    an enclosure capable of containing an experimental animal and permitting the inspection of events occurring therewithin by the human eye, said enclosure being positioned on the top surface of said base after depositing said animal on the surface, whereby said base and said enclosure define said predetermined space within which said animal remains unrestrained.

8. The apparatus claim 2, wherein said light beam window is located in a side wall of said container.

* * * * *